US010617339B2

(12) United States Patent
Yamaguchi et al.

(10) Patent No.: US 10,617,339 B2
(45) Date of Patent: Apr. 14, 2020

(54) ENDOSCOPE SYSTEM

(71) Applicant: FUJIFILM Corporation, Tokyo (JP)

(72) Inventors: Hiroshi Yamaguchi, Ashigarakami-gun (JP); Yoshinori Morimoto, Ashigarakami-gun (JP); Takumi Dejima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 661 days.

(21) Appl. No.: 14/697,763

(22) Filed: Apr. 28, 2015

(65) Prior Publication Data
US 2015/0313517 A1 Nov. 5, 2015

Related U.S. Application Data

(63) Continuation of application No. PCT/JP2013/078405, filed on Oct. 21, 2013.

(30) Foreign Application Priority Data

Nov. 8, 2012 (JP) .................................. 2012-246448

(51) Int. Cl.
A61B 1/00 (2006.01)
A61B 17/04 (2006.01)
(Continued)

(52) U.S. Cl.
CPC .......... A61B 5/1459 (2013.01); A61B 1/0005 (2013.01); A61B 1/00009 (2013.01);
(Continued)

(58) Field of Classification Search
CPC .. A61B 5/1455; A61B 5/14551; A61B 5/1459
See application file for complete search history.

(56) References Cited

U.S. PATENT DOCUMENTS 6,594,518 B1 *  7/2003  Benaron ............. A61B 5/1459
                                                     600/342
2009/0054908 A1 *  2/2009  Zand ................... A61B 5/1459
                                                     600/300
(Continued)

FOREIGN PATENT DOCUMENTS

JP           5-49624 A      3/1993
JP        2005-204694 A     8/2005
(Continued)

OTHER PUBLICATIONS

Japanese Notification of Reasons for Refusal for Japanese Application No. 2012-246448, dated May 6, 2016, with a Machine Translation thereof.
International Search Report issued in PCT/JP2013/078405, dated Nov. 26, 2013.
PCT/ISA/237—Issued in PCT/JP2013/078405, mailed on Nov. 26, 2013.

Primary Examiner — Eric F Winakur
(74) Attorney, Agent, or Firm — Birch, Stewart, Kolasch & Birch, LLP

(57) ABSTRACT

The invention provides an endoscope system for generating an oxygen saturation image that can be used for various medical applications, such as oxygen saturation monitoring during surgery. A clip 141 is attached to the surrounding tissue of a tumor CN from the luminal side. The tissue to which the clip 141 is attached becomes an ischemic part CL. An oxygen saturation image is generated from image information obtained by imaging the tissue on the abdominal cavity side. In the oxygen saturation image, the ischemic part CL is displayed as a low oxygen region. Accordingly, it becomes easy to find the location of the tumor CN even from the abdominal cavity side.

22 Claims, 58 Drawing Sheets

(51) Int. Cl.

| | |
|---|---|
| *A61B 5/00* | (2006.01) |
| *A61B 5/1459* | (2006.01) |
| *A61B 5/1455* | (2006.01) |
| *A61B 1/05* | (2006.01) |
| *A61B 1/313* | (2006.01) |
| *A61B 1/06* | (2006.01) |
| *A61B 5/145* | (2006.01) |
| *A61B 1/04* | (2006.01) |
| *A61B 1/045* | (2006.01) |

(52) U.S. Cl.
CPC .............. *A61B 1/043* (2013.01); *A61B 1/045* (2013.01); *A61B 1/05* (2013.01); *A61B 1/0638* (2013.01); *A61B 1/0669* (2013.01); *A61B 1/3132* (2013.01); *A61B 5/1455* (2013.01); *A61B 5/14542* (2013.01)

(56) References Cited

U.S. PATENT DOCUMENTS

| | | | |
|---|---|---|---|
| 2010/0185220 A1* | 7/2010 | Naghavi | A61B 5/14546 600/301 |
| 2011/0071352 A1* | 3/2011 | Ozawa | A61B 1/0638 600/109 |
| 2011/0237915 A1* | 9/2011 | Yamaguchi | A61B 5/14551 600/339 |
| 2012/0179013 A1 | 7/2012 | Saito | |
| 2013/0289373 A1 | 10/2013 | Yamamoto | |

FOREIGN PATENT DOCUMENTS

| | | |
|---|---|---|
| JP | 2012-135431 A | 7/2012 |
| JP | 2012-143399 A | 8/2012 |

* cited by examiner

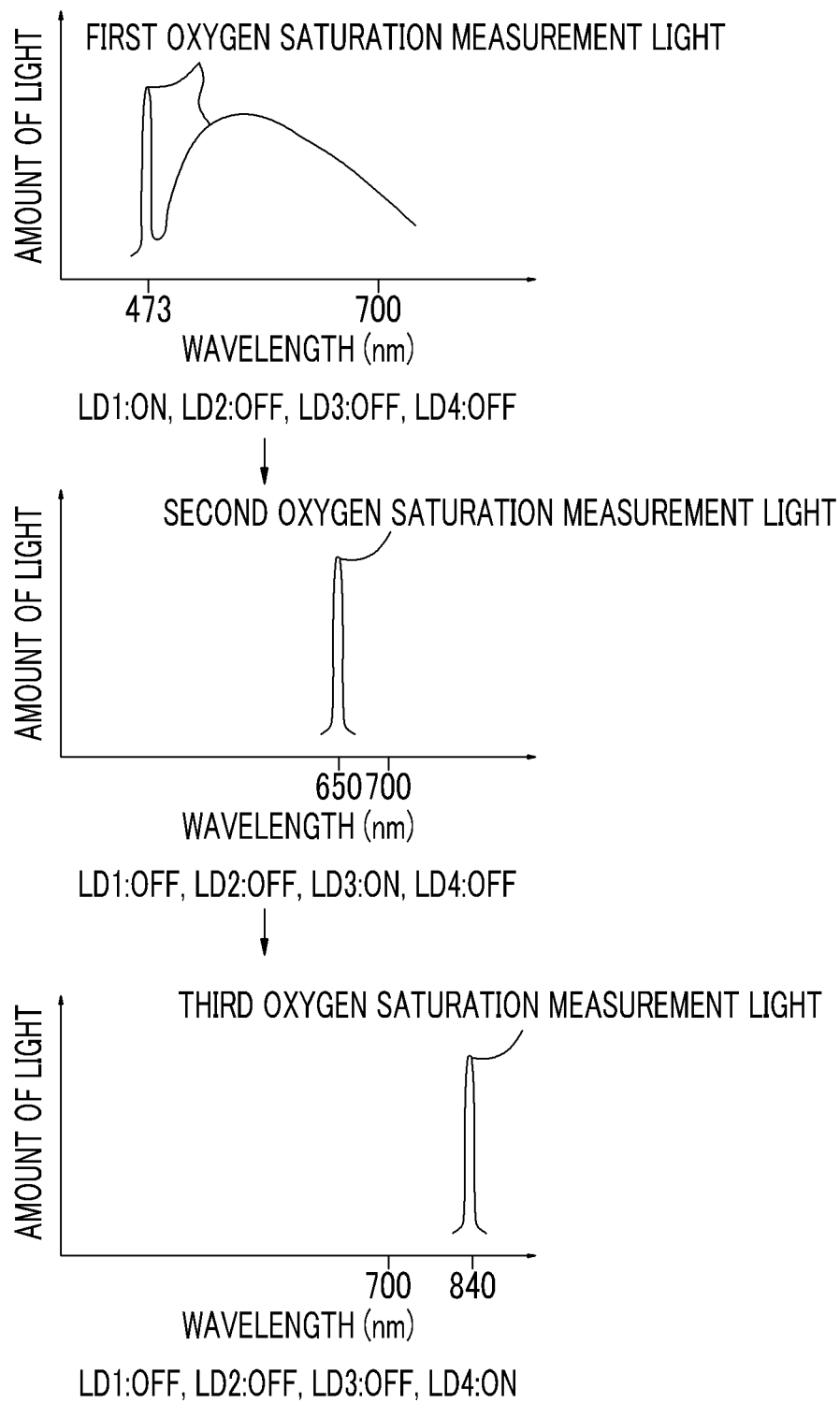

"TISSUES ARE NOT FUSED"

(CONT.)

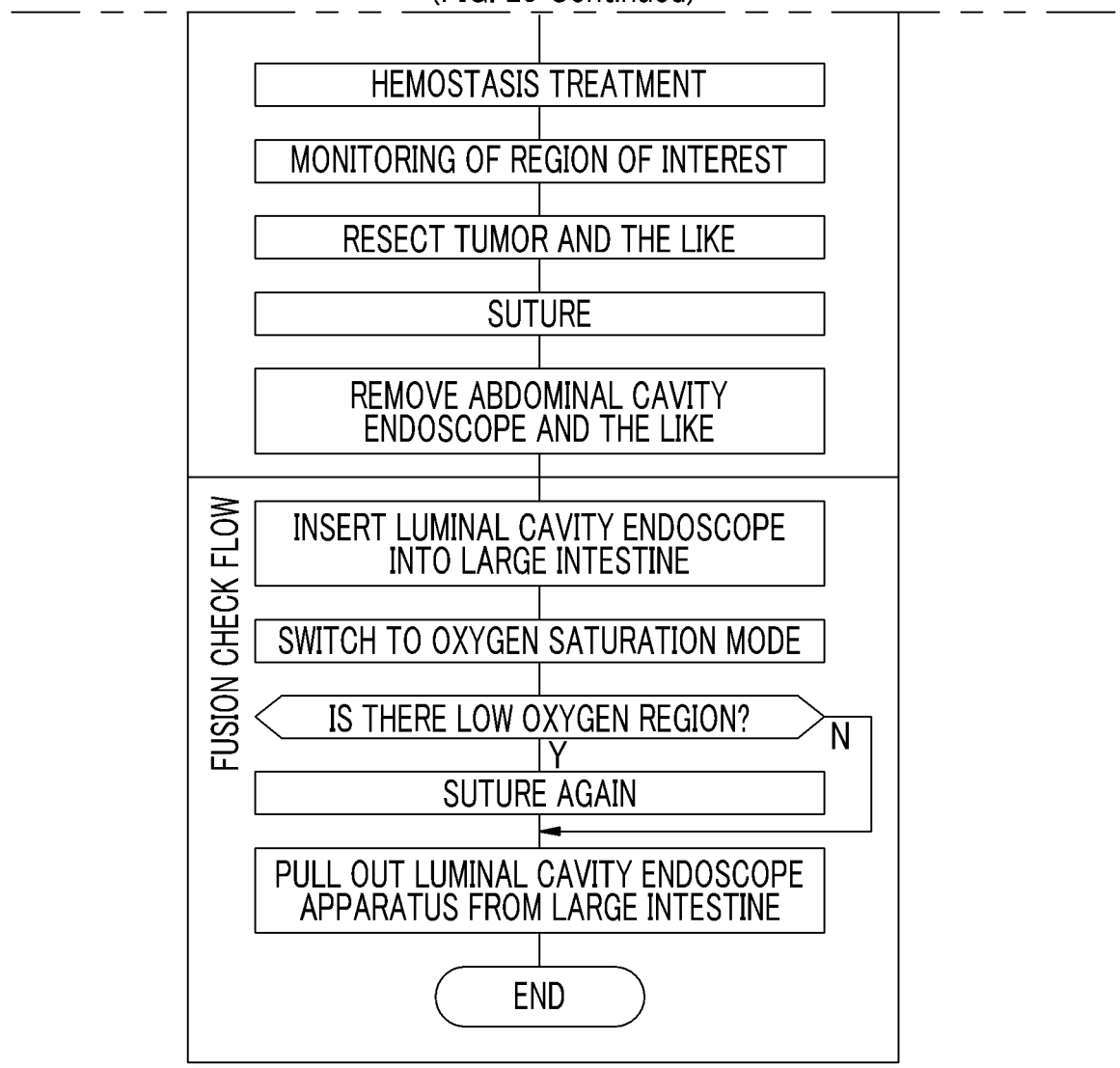

ENDOSCOPE SYSTEM

CROSS REFERENCE TO RELATED APPLICATIONS

This application is a Continuation of PCT International Application No. PCT/JP2013/078405 filed on Oct. 21, 2013, which claims priority under 35 U.S.C § 119(a) to Patent Application No. 2012-246448 filed in Japan on Nov. 8, 2012, all of which are hereby expressly incorporated by reference into the present application.

BACKGROUND OF THE INVENTION

1. Field of the Invention

The present invention relates to an endoscope system that is used during surgery to resect a tumor, such as cancer, or before the surgery.

2. Description of the Related Art

In recent years, laparoscopic surgery to perform an operation using a laparoscope has been drawing attention. In the laparoscopic surgery, a laparoscope and surgical treatment tools are inserted into an abdominal cavity through two or three trocars provided in the abdomen of the patient, and the abdominal cavity is inflated with pneumoperitoneum gas made of carbon dioxide. Then, the operator performs various operations using the surgical treatment tools while observing an image of the abdominal cavity displayed on the monitor. Thus, for the laparoscopic surgery, it is necessary to perform operations in the limited field of view of the laparoscope. Accordingly, a high level of skill is required for the operator. However, since there is no need for laparotomy, unlike in general surgery, the burden on the patient is considerably reduced. When performing such laparoscopic surgery, the oxygen saturation of a region of interest is monitored using an oxygen saturation monitoring device (for example, refer to JP1993-49624A (JP-H05-49624A)), such as a pulse oximeter, so that the tissue in the region of interest does not fall into a low oxygen state.

SUMMARY OF THE INVENTION

With the oxygen saturation monitoring device disclosed in JP1993-49624A (JP-H05-49624A), only the oxygen saturation at a predetermined position in the region of interest can be measured. For this reason, a low oxygen state may occur at a different position from the predetermined position. Therefore, it has been demanded to display the oxygen saturation distribution of the entire region of interest as an image in real time. If the spatial distribution of the oxygen saturation can be displayed as an image, it can be used for various medical applications, such as the detection of cancer in a low oxygen state, as well as oxygen saturation monitoring during surgery.

It is an object of the invention to provide an endoscope system capable of generating an oxygen saturation image that can be used for various medical applications, such as oxygen saturation monitoring during surgery and the detection of cancer in a low oxygen state.

In order to achieve the aforementioned object, an endoscope system of the invention includes: a treatment tool for making a tissue in a subject fall into an ischemic state; an imaging unit that images the tissue in the ischemic state; an oxygen saturation distribution image generation unit that generates an oxygen saturation distribution image showing an oxygen state of the tissue in the ischemic state based on image information obtained by the imaging unit; and a display unit that displays the oxygen saturation distribution image.

Preferably, the treatment tool is attached to a region around a tumor in a lumen, and the oxygen saturation distribution image is displayed when identifying a location of the tumor from an abdominal cavity side. Preferably, the treatment tool is at least one of a clip and a catheter for blood vessel occlusion. Preferably, the treatment tool is used for hemostasis of a first blood vessel connected to a tumor, and the oxygen saturation distribution image generation unit includes an image generation section that generates the oxygen saturation distribution image and a determination section that determines whether or not blood flow in the first blood vessel has stopped based on the oxygen saturation distribution image. Preferably, the display unit displays a determination result of the determination section. It is preferable to further include a monitoring unit for monitoring an oxygen state of a second blood vessel, which is not resected during predetermined surgery, of the tissue based on the image information obtained by the imaging unit.

Preferably, the oxygen saturation distribution image generation unit generates the oxygen saturation distribution image based on first image information, which includes wavelength components at which an absorption coefficient of oxygenated hemoglobin and an absorption coefficient of reduced hemoglobin are different, and second image information including wavelength components that are different from the wavelength components in the first image. Preferably, the oxygen saturation distribution image generation unit includes an oxygen saturation calculation section that calculates an oxygen saturation of each pixel based on the first and second image information and an oxygen saturation distribution image generation section that generates the oxygen saturation distribution image based on the oxygen saturation.

It is preferable to further include an illumination unit that emits illumination light toward the tissue in the ischemic state, the illumination light including light of a semiconductor light source and fluorescent light obtained by wavelength conversion of the light of the semiconductor light source. Preferably, the imaging unit images the tissue in the ischemic state with a color imaging device. Preferably, the imaging unit images a subject, to which a plurality of illumination light beams in different wavelength bands are sequentially emitted, with a monochrome imaging device.

According to the invention, a variety of diagnoses or treatments in surgery and the like can be realized by the combination of the treatment tool for making the tissue in the subject fall into the ischemic state and the oxygen saturation distribution image showing the oxygen saturation distribution of the tissue that has fallen into the ischemic state by the treatment tool. For example, before surgery using a laparoscope, if the treatment tool is attached to the surrounding tissue of a tumor on the luminal side so that the surrounding tissue falls into the ischemic state, the tissue in the ischemic state can be displayed as a low oxygen region in the oxygen saturation image captured from the abdominal cavity side. Therefore, if the oxygen saturation image is used, it becomes easy to find the location of the tumor even from the abdominal cavity side.

In addition, during the hemostasis performed when resecting a tumor, the first blood vessel in which the blood flow has stopped is in the ischemic state. Accordingly, the blood vessel in which the blood flow has stopped is displayed as a low oxygen region in the oxygen saturation image. Therefore, it is possible to check whether or not blood flow has stopped completely in the oxygen saturation image. In addition, during tumor surgery, by monitoring the oxygen state of the second blood vessel that is left without being resected, it is possible to check the damage of the surrounding tissue of the second blood vessel.

BRIEF DESCRIPTION OF THE DRAWINGS

FIG. 4C is an explanatory diagram showing the emission pattern in a fusion check mode.

DESCRIPTION OF THE PREFERRED EMBODIMENTS

Figure 1:
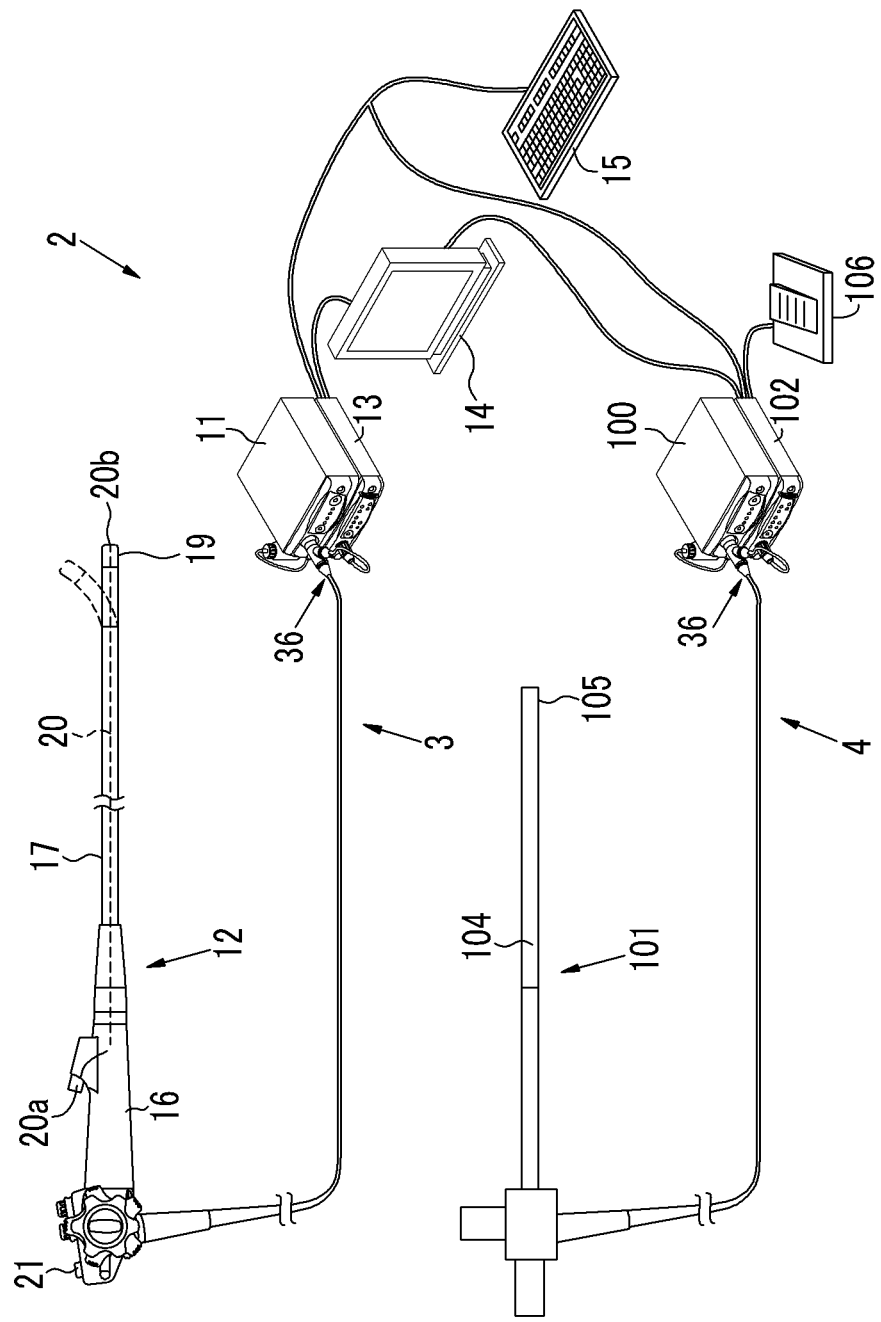
FIG. 1 is an external view of a medical apparatus system.

As shown in FIG. 1, a medical apparatus system 2 of a first embodiment is configured to include a luminal cavity endoscope system 3 and an abdominal cavity endoscope system 4, and is used to resect a tumor generated in the large intestine. First, using the luminal cavity endoscope system 3, a tumor in the large intestine is detected and a mark is put on a predetermined range (resection range) including the tumor before the resection of the tumor. Then, using the abdominal cavity endoscope system 4, the resection range with a mark in the large intestine is resected, and the large intestine cut by the resection of the tumor is sutured. Finally, using the luminal cavity endoscope system 3, it is checked whether or not the tissues of the sutured portion are fused.

The luminal cavity endoscope system 3 includes a luminal cavity light source device 11 that generates light for illuminating the lumen, a luminal cavity endoscope apparatus 12 that emits the light from the luminal cavity light source device 11 toward the lumen and captures the reflected image, and a luminal cavity processor device 13 that performs image processing on image signals obtained by imaging using the luminal cavity endoscope apparatus 12. The luminal cavity processor device 13 is connected to a display device 14 for displaying an endoscope image obtained by image processing and an input device 15 formed by a keyboard or the like.

The luminal cavity endoscope apparatus 12 is a flexible endoscope, and includes an operating unit 16, a flexible insertion unit 17, and a scope tip portion 19 that is provided at the tip of the insertion unit and that emits light toward the lumen and captures a reflected image of the lumen. In the luminal cavity endoscope apparatus 12, a forceps channel 20 for inserting a treatment tool, such as a hemostatic probe, is provided. The treatment tool is inserted into the forceps channel 20 from a forceps inlet 20a provided in the operating unit, and the treatment tool inserted into the forceps channel 20 protrudes from a forceps outlet 20b in the tip portion (refer to FIG. 3).

The luminal cavity endoscope system 3 has a normal mode, an oxygen saturation mode, and a fusion check mode. In the normal mode, a normal image formed as a subject image of visible light having a wavelength range from blue to red is displayed on the display device 14. In the oxygen saturation mode, an oxygen saturation image obtained by imaging the oxygen saturation of blood hemoglobin is displayed on the display device 14. The fusion check mode is a mode for checking the extent of fusion of tissues connected together by suturing from the oxygen saturation image. These three modes can be switched by using a selector switch 21a provided in the luminal cavity endoscope apparatus. In addition, the luminal cavity endoscope system 3 has an automatic determination mode for automatically determining the extent of fusion in the luminal cavity processor device 13. ON and OFF of the automatic determination mode can be switched by the input device 15.

The abdominal cavity endoscope system 4 includes an abdominal cavity light source device 100 that generates light for illuminating an abdominal cavity, an abdominal cavity endoscope apparatus 101 that emits the light from the abdominal cavity light source device 100 toward the abdominal cavity and captures the reflected image, and an abdominal cavity processor device 102 that performs image processing on image signals obtained by imaging using the abdominal cavity endoscope apparatus 101. The abdominal cavity processor device 102 is connected to the display device 14 and the input device 15. The abdominal cavity endoscope apparatus 101 is a rigid endoscope, and includes a rigid insertion unit 104 and a tip portion 105 that is provided at the tip of the insertion unit and that emits light toward the abdominal cavity and captures a reflected image of the abdominal cavity.

The abdominal cavity endoscope system 4 has an infiltration check mode for checking the extent of infiltration of a tumor in addition to the normal mode and the oxygen saturation mode that are the same as in the luminal cavity endoscope system 3. These three modes can be switched by using a foot switch 106 connected to the abdominal cavity processor device 102. In addition, the luminal cavity endoscope system 3 has an automatic determination mode for automatically determining the extent of infiltration or lymph node metastasis in the abdominal cavity processor device 102. ON and OFF of the automatic determination mode can be switched by the input device 15.

Figure 2:
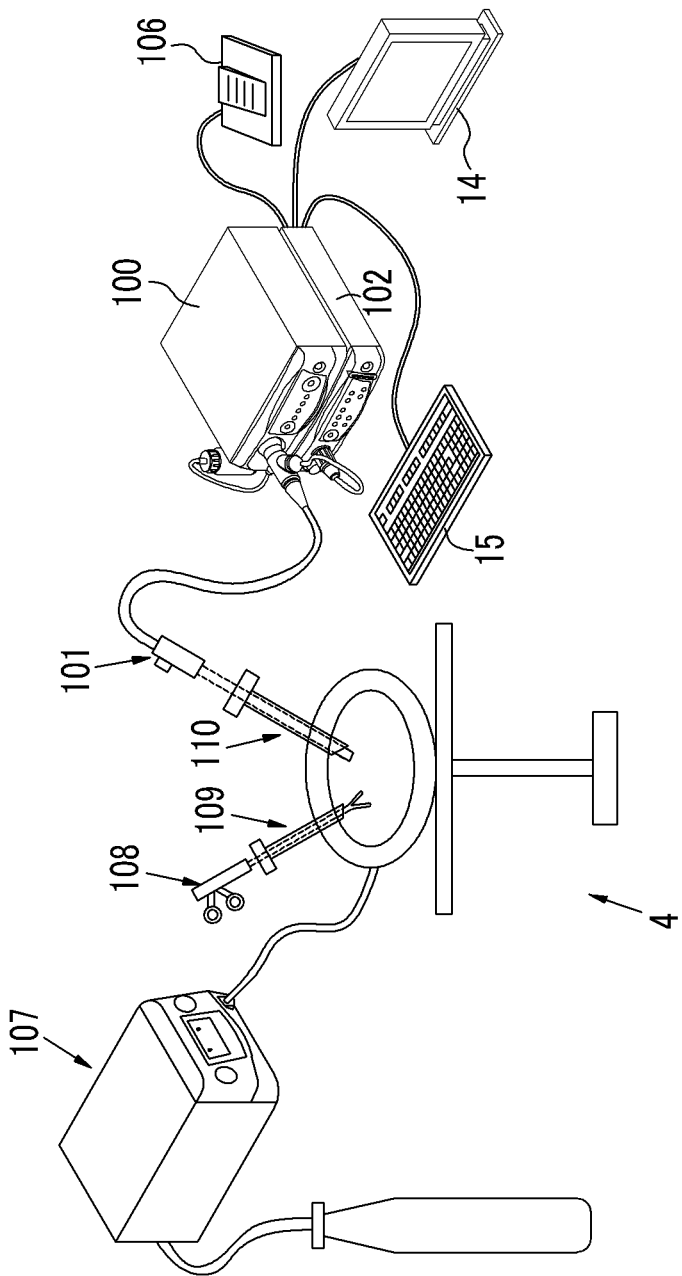
FIG. 2 is an external view of an abdominal cavity endoscope system.

As shown in FIG. 2, in the abdominal cavity endoscope system 4, in order to perform the observation of the abdominal cavity and tumor extirpation surgery, not only the abdominal cavity light source device 100, the abdominal cavity endoscope apparatus 101, and the abdominal cavity processor device 102 but also a pneumoperitoneum device 107, a treatment tool 108, and trocars 109 and 110 are used. In the abdominal cavity endoscope system 4, first, $CO_2$ is supplied to the abdominal cavity from the pneumoperitoneum device, thereby performing abdominal pneumoperitoneum. Therefore, it is possible to ensure the field of view for surgery in the abdominal cavity.

Then, each treatment tool 108 is inserted into the abdominal cavity through the trocar 109, and the abdominal cavity endoscope apparatus 101 is inserted into the abdominal cavity through the trocar 110. Each of the trocars 109 and 110 includes a metal hollow tube and an operator gripping portion. When the operator inserts a sharp-shaped tip of the hollow tube into the abdominal cavity while holding the operator gripping portion, the hollow tube is inserted into the body cavity. For the trocars 109 and 110 whose hollow tubes have been inserted into the abdominal cavity as described above, the treatment tool 108 and the abdominal cavity endoscope apparatus 101 are inserted.

Figure 3:
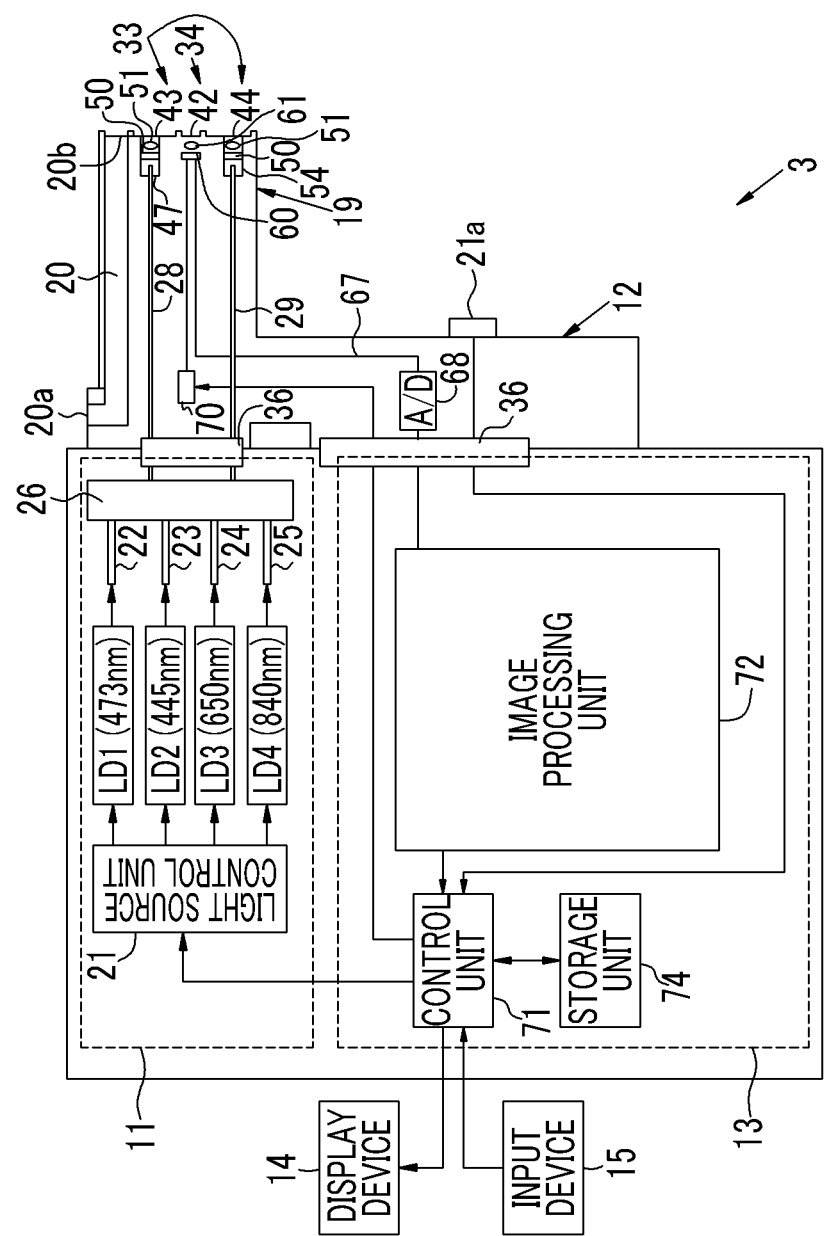
FIG. 3 is a block diagram of a luminal cavity endoscope system.

As shown in FIG. 3, the luminal cavity light source device 11 includes four kinds of laser light sources LD1, LD2, LD3, and LD4 and a light source control unit 21. The laser light source LD1 emits a first laser beam having a center wavelength of 473 nm. The first laser beam is wavelength-converted into fluorescent light having a wavelength range from green to red by a fluorescent body 50 (wavelength conversion member) disposed in the scope tip portion 19 of the endoscope apparatus 12. The laser light source LD2 emits a second laser beam having a center wavelength of 445 nm. The second laser beam is also wavelength-converted into fluorescent light by the fluorescent body 50. The laser light source LD3 emits a third laser beam having a center wavelength of 650 nm. The third laser beam is transmitted through the fluorescent body 50 without being absorbed by the fluorescent body 50. The laser light source LD4 emits a fourth laser beam having a center wavelength of 840 nm.

The fourth laser beam is also transmitted through the fluorescent body 50 without being absorbed by the fluorescent body 50.

The first to fourth laser beams emitted from the laser light sources LD1 to LD4 are incident on optical fibers 22 to 25 through a condensing lens (not shown), respectively. The wavelength range of the first laser beam is preferably set to 460 nm to 480 nm, the wavelength range of the second laser beam is preferably set to 440 nm 460 nm, the wavelength range of the third laser beam is preferably set to 640 nm 660 nm, and the wavelength range of the fourth laser beam is preferably set to 830 nm to 850 nm. As the laser light sources LD1 to LD4, a broad area type InGaN-based laser diode can be used, or an InGaNAs-based laser diode or a GaNAs-based laser diode can be used.

The light source control unit 21 controls the driving of the laser light sources LD1 to LD4. A coupler 26 demultiplexes the first to fourth laser beams from the optical fibers 22 to 25 into light beams of two systems, and the light beams of two systems are incident on light guides 28 and 29. Each of the light guides 28 and 29 is formed by a fiber bundle obtained by bundling a large number of optical fibers.

The luminal cavity endoscope apparatus 12 is an electronic endoscope, and includes an illumination unit 33 for emitting the light beams of two systems (two lamps) guided by the light guides 28 and 29 toward a region to be observed, an imaging unit 34 for imaging the region to be observed, and a connector unit 36 for removably connecting the luminal cavity endoscope apparatus 12 to the luminal cavity light source device 11 and the luminal cavity processor device 13.

The illumination unit 33 includes two illumination windows 43 and 44 provided in both sides of the imaging unit 34, and each of the illumination windows 43 and 44 emits light transmitted through the fluorescent body 50 toward the region to be observed. The imaging unit 34 includes one observation window 42 for receiving light reflected from the region to be observed, the observation window 42 being located at the approximate center position of the scope tip portion 19.

Light projection units 47 and 54 are housed behind the illumination windows 43 and 44. The light projection units 47 and 54 make light from the light guides 28 and 29 incident on the fluorescent body 50. Among the laser beams incident on the fluorescent body 50, the first and second laser beams are wavelength-converted into fluorescent light by the fluorescent body 50, while the third and fourth laser beams are transmitted through the fluorescent body 50 without being absorbed by the fluorescent body 50. The light emitted from the fluorescent body 50 is emitted toward the region to be observed through a lens 51.

The fluorescent body 50 is configured to contain a plurality of kinds of fluorescent materials (for example, a YAG-based fluorescent material or a fluorescent material, such as BAM ($BaMgAl_{10}O_{17}$)) that are excited to emit light of green to red by absorbing some of the first and second laser beams. When the first and second laser beams are emitted to the fluorescent body 50, excitation light (fluorescent light) of green to red emitted from the fluorescent body 50 and excitation light of the first and second laser beams transmitted through the fluorescent body 50 without being absorbed by the fluorescent body 50 are combined with each other. As a result, pseudo-white light is generated.

Preferably, the fluorescent body 50 has an approximately rectangular parallelepiped shape. In this case, the fluorescent body 50 may be formed by solidifying a fluorescent material in the approximately rectangular parallelepiped shape using a binder. Alternatively, the fluorescent body 50 may be formed by forming a mixture of a fluorescent material and a resin, such as inorganic glass, in the approximately rectangular parallelepiped shape. The fluorescent body 50 is also referred to as Micro White (MW) (registered trademark) as a product name.

An objective lens unit 61 for capturing image light of the region to be observed of the subject is provided behind the observation window 42. In addition, an imaging device 60 such as a charge coupled device (CCD) for receiving the image light of the region to be observed and imaging the region to be observed is provided behind the objective lens unit 61. As the imaging device 60, an interline transfer (IT) type CCD is used. However, it is also possible to use a complementary metal-oxide semiconductor (CMOS) having a global shutter.

The imaging device 60 receives light from the objective lens unit 61 on the light receiving surface (imaging surface), performs photoelectric conversion of the received light, and outputs an imaging signal (analog signal). The imaging control of the imaging device 60 is performed by an imaging control unit 70. The imaging signal (analog signal) output from the imaging device 60 is input to an A/D converter 68 through a scope cable 67. The A/D converter 68 converts the imaging signal (analog signal) into image data (digital signal) corresponding to the voltage level. The image data after conversion is input to the luminal cavity processor device 13 through the connector unit 36.

The luminal cavity processor device 13 includes a control unit 71, an image processing unit 72, and a storage unit 74, and the display device 14 and the input device 15 are connected to the control unit 72. The control unit 72 controls each unit of the luminal cavity processor device 13, and controls the operations of the light source control unit 21 of the luminal cavity light source device 11, the imaging control unit 70 of the luminal cavity endoscope apparatus 12, and the display device 14 based on input information that is input from the selector switch 21a of the luminal cavity endoscope apparatus 12 or the input device 15.

Figure 4A:
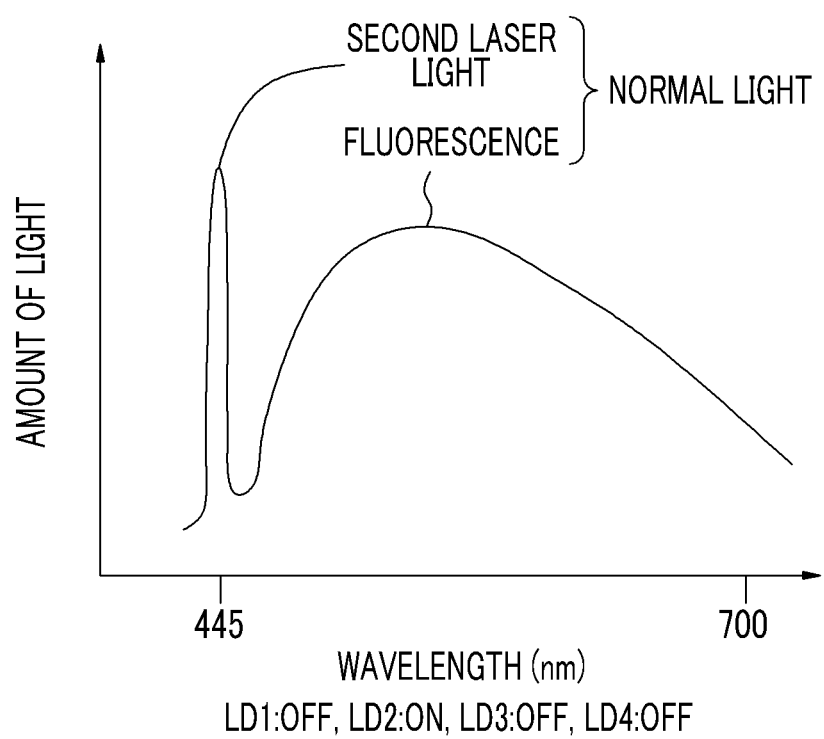
FIG. 4A is an explanatory diagram showing the emission pattern in a normal mode.
Figure 4B:
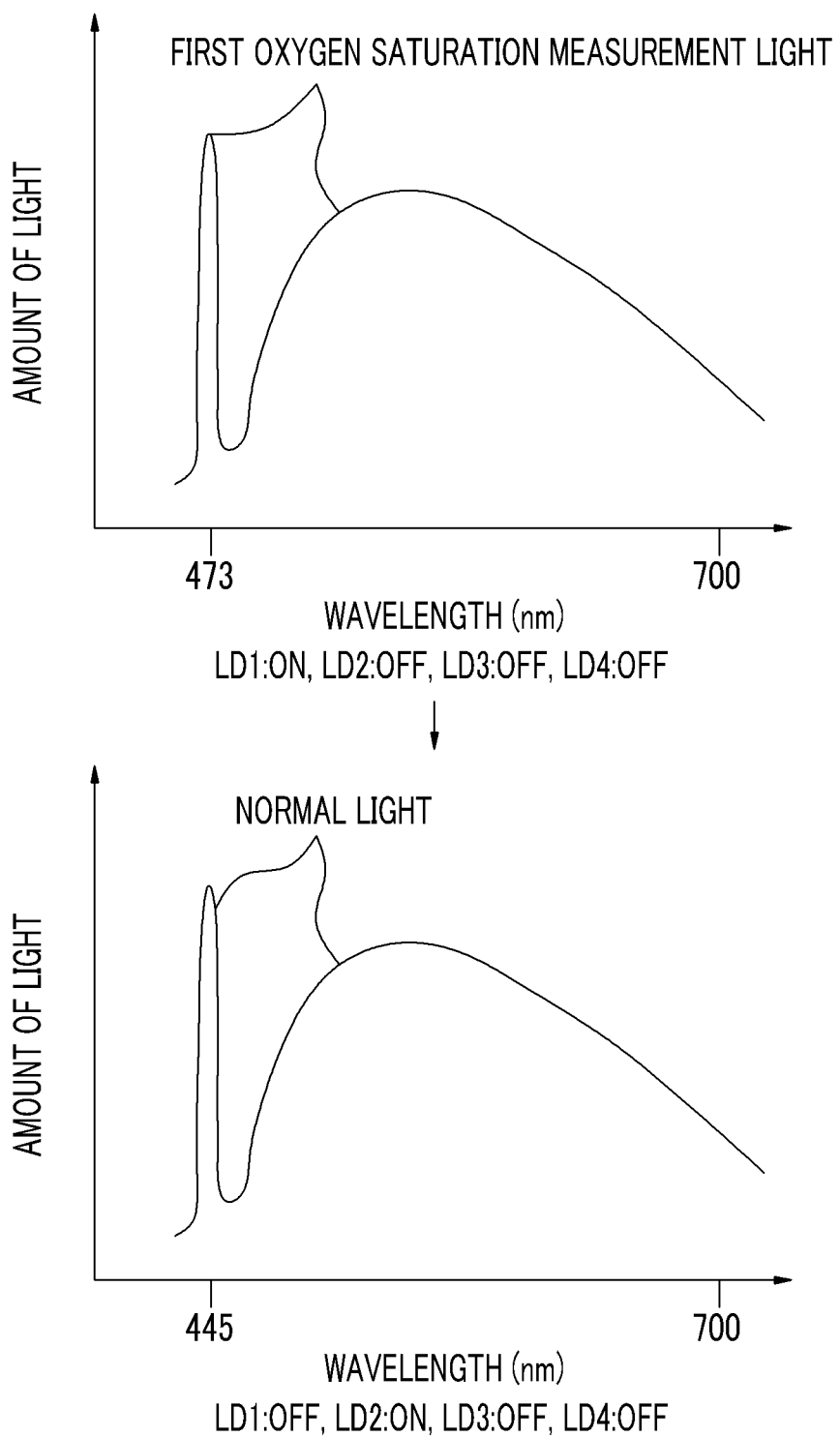
FIG. 4B is an explanatory diagram showing the emission pattern in an oxygen saturation mode.

The light source control unit 21 of the luminal cavity light source device 11 performs different driving control for each mode. In the normal mode, as shown in FIG. 4A, the laser light source LD2 is turned on, and the laser light sources LD1, LD3, and LD4 are turned off. As a result, normal light including the second laser beam of the laser light source LD2 and fluorescent light are emitted to the inside of the subject. In the oxygen saturation mode, as shown in FIG. 4B, emission control to repeat ON and OFF of the laser light sources LD1 and LD2 alternately is performed in a state where the laser light sources LD3 and 4 are turned off. As a result, first oxygen saturation measurement light including the first laser beam of the laser light source LD1 and fluorescent light, which is generated due to excitation of the fluorescent body 50 by the first laser beam, and the normal light are alternately emitted to the inside of the subject.

In the fusion check mode, as shown in FIG. 4C, emission control to turn on the laser light sources LD1, LD3, and LD4 in a sequential manner is performed in a state where the laser light source LD2 is turned off. As a result, the first oxygen saturation measurement light, second oxygen saturation measurement light of the third laser beam, and third oxygen saturation measurement light of the fourth laser beam are sequentially emitted to the inside of the subject.

Figure 5A:
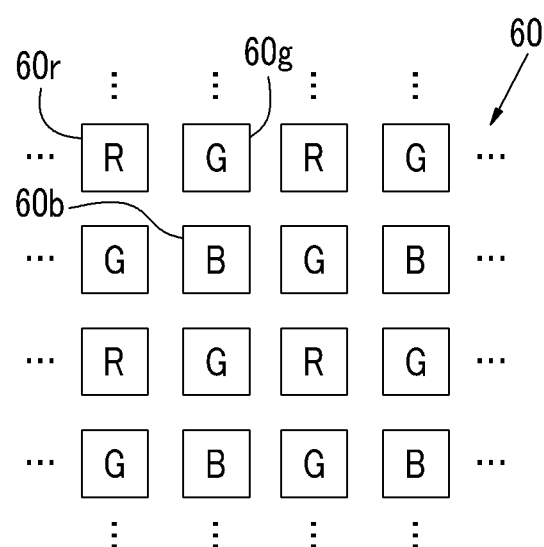
FIG. 5A is a plan view showing B, G, and R pixels of a color imaging device.
Figure 5B:
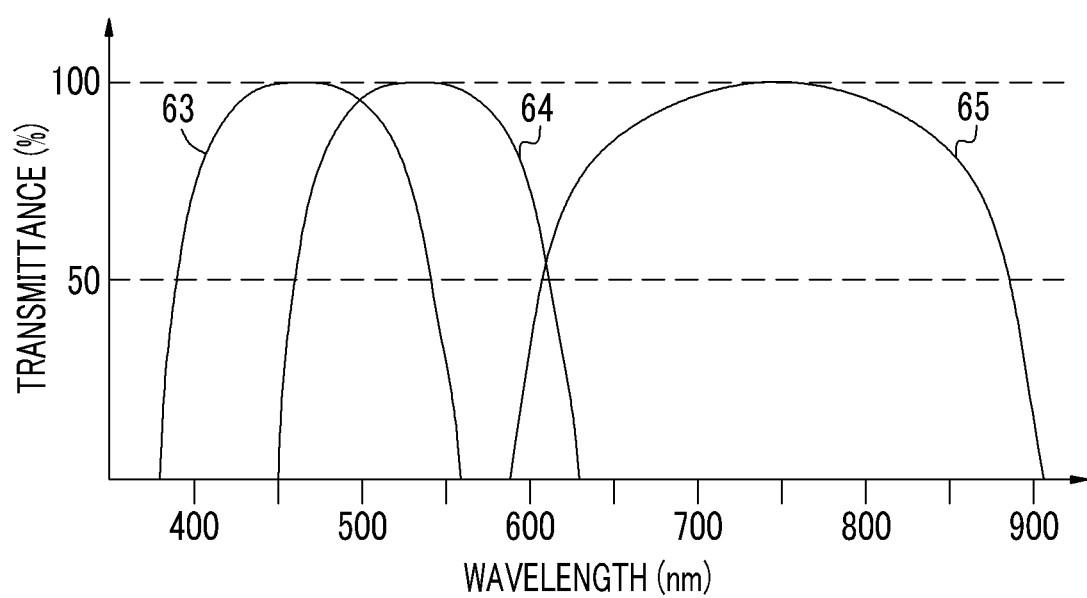
FIG. 5B is a graph showing the spectral transmittances of color filters of B, G, and R colors.

The imaging device 60 provided in the luminal cavity endoscope apparatus 12 is a color CCD. As shown in FIG. 5A, a pixel group having a B pixel 60b, a G pixel 60g, and an R pixel 60r as one set is arranged in a matrix on the light receiving surface. A color filter of B color is provided in the B pixel 60b, a color filter of G color is provided in the G pixel 60g, and a color filter of R color is provided in the R pixel 60r. The color filters of B, G, and R colors have spectral transmittances in a blue band, a green band, and a red band and a near-infrared band, respectively, as shown in curves 63, 64, and 65 of FIG. 5B.

Figure 6A:
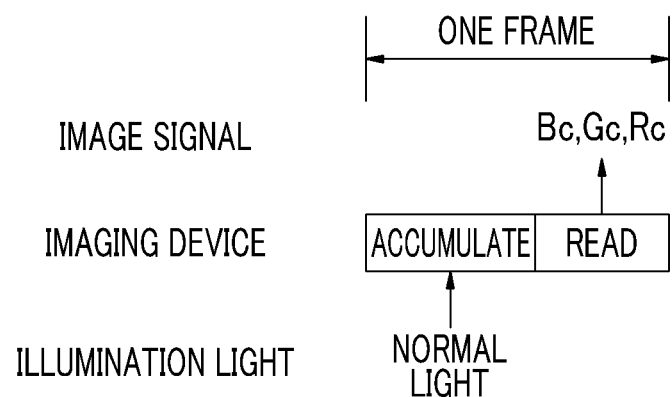
FIG. 6A is a diagram for explaining the imaging control in the normal mode in a first embodiment.

Since different light source control is performed for each mode as described above, the imaging control unit 70 also performs different imaging control for each mode. In the normal mode, as shown in FIG. 6A, a step of accumulating electric charges after performing photoelectric conversion of the normal light with the imaging device 60 and a step of reading a blue signal Bc, a green signal Gc, and a red signal Rc from the B, G, and R pixels of the imaging device 60 are performed in one frame period. This is repeatedly performed while the normal mode is set. The blue signal Bc, the green signal Gc, and the red signal Rc are converted into blue image data Bc, green image data Gc, and red image data Rc, respectively, by the A/D converter 68.

Figure 6B:
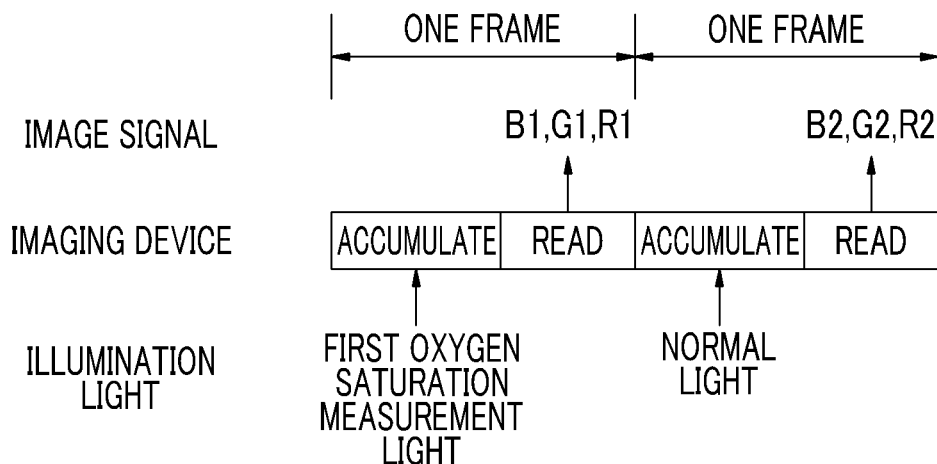
FIG. 6B is a diagram for explaining the imaging control in the oxygen saturation mode in the first embodiment.

In the oxygen saturation mode, as shown in FIG. 6B, a step of accumulating electric charges after performing photoelectric conversion of the oxygen saturation measurement light with the imaging device 60 and a step of reading a blue signal B1, a green signal G1, and a red signal R1 from the B, G, and R pixels of the imaging device 60 are performed in the first frame. Then, in the next second frame, a step of accumulating electric charges after performing photoelectric conversion of the normal light with the imaging device 60 and a step of reading a blue signal B2, a green signal G2, and a red signal R2 from the B, G, and R pixels of the imaging device 60 are performed. This imaging control of a total of two frames is repeatedly performed while the oxygen saturation mode is set.

The blue signal B1, the green signal G1, and the red signal R1 are converted into blue image data B1, green image data G1, and red image data R1, respectively, by the A/D converter 68, and the blue signal B2, the green signal G2, and the red signal R2 are converted into blue image data B2, green image data G2, and red image data R2, respectively, by the A/D converter 68.

Figure 6C:
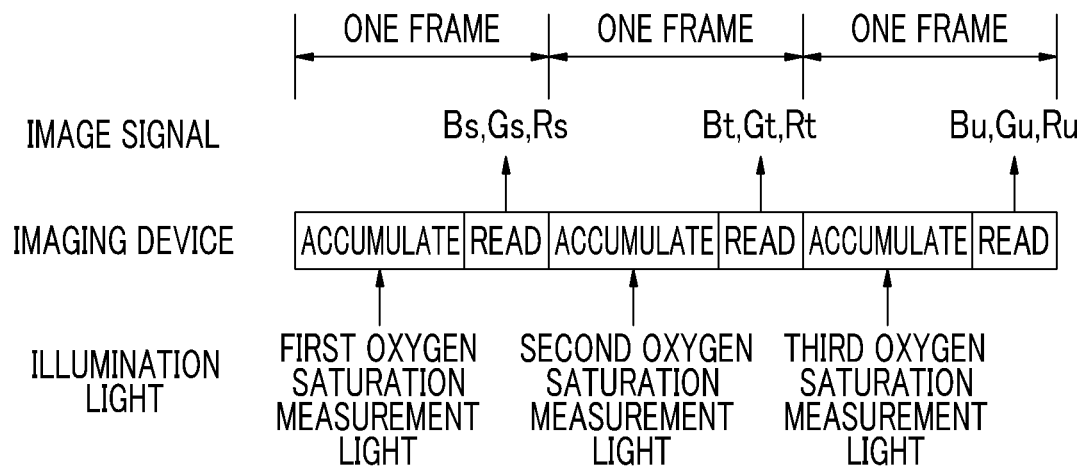
FIG. 6C is a diagram for explaining the imaging control in the fusion check mode in the first embodiment.

In the fusion check mode, as shown in FIG. 6C, first, a step of accumulating electric charges after performing photoelectric conversion of the first oxygen saturation measurement light with the imaging device 60 and a step of reading a blue signal Bs, a green signal Gs, and a red signal Rs from the imaging device 60 are performed in the first frame. Then, in the second frame, a step of accumulating electric charges after performing photoelectric conversion of the second oxygen saturation measurement light with the imaging device 60 and a step of reading a blue signal Bt, a green signal Gt, and a red signal Rt from the imaging device 60 are performed. Then, in the third frame, a step of accumulating electric charges after performing photoelectric conversion of the third oxygen saturation measurement light with the imaging device 60 and a step of reading a blue signal Bu, a green signal Gu, and a red signal Ru from the imaging device 60 are performed. This imaging control of a total of three frames is repeatedly performed while the fusion check mode is set.

The blue signal Bs, the green signal Gs, and the red signal Rs are converted into blue image data Bs, green image data Gs, and red image data Rs, respectively, by the A/D converter 68. The blue signal Bt, the green signal Gt, and the red signal Rt are converted into blue image data Bt, green image data Gt, and red image data Rt, respectively, by the A/D converter 68. The blue signal Bu, the green signal Gu, and the red signal Ru are converted into blue image data Bu, green image data Gu, and red image data Ru, respectively, by the A/D converter 68.

Figure 7:
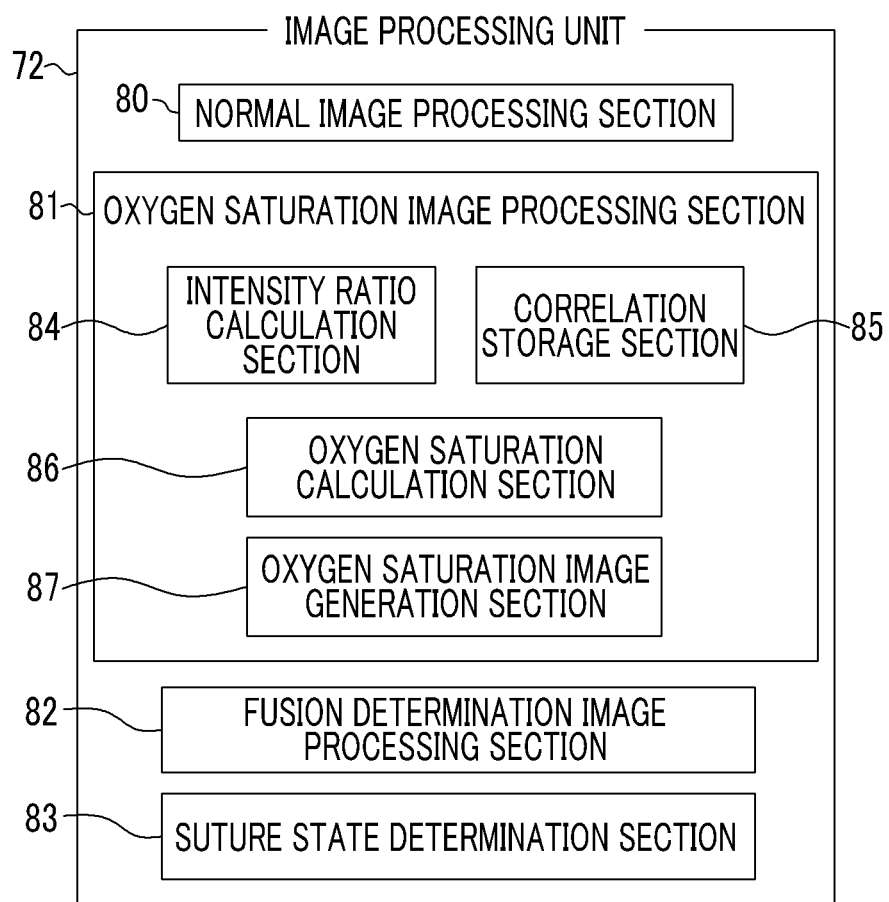
FIG. 7 is a block diagram showing an image processing unit in a luminal cavity processor device.

As shown in FIG. 7, the image processing unit 72 includes a normal image processing section 80, an oxygen saturation image processing section 81, a fusion determination image processing section 82, and a suture state determination section 83. The normal image processing section 80 performs processing for assigning the blue image data Bc, the green image data Gc, and the red image data Rc obtained in the normal mode to B, G, and R channels of the display device 14, respectively. As a result, a normal image is displayed on the display device 14.

The oxygen saturation image processing section 81 includes an intensity ratio calculation section 84, a correlation storage section 85, an oxygen saturation calculation section 86, and an oxygen saturation image generation section 87. The intensity ratio calculation section 84 calculates the intensity ratio B1/G2 between the blue image data B1 and the green image data G2 and the intensity ratio R2/G2 between the green image data G2 and the red image data R2 among the pieces of image data obtained in the oxygen saturation mode. The intensity ratio calculation section 84 calculates the intensity ratio between pixels at the same position in the respective pieces of image data, and the intensity ratio is calculated for all pixels of the image data. Alternatively, the intensity ratio may be calculated only for pixels of a blood vessel portion of the image data. In this case, the blood vessel portion is identified based on the difference between the pixel values of pixels of the blood vessel portion and the pixel values of pixels of the other portions.

Figure 8:
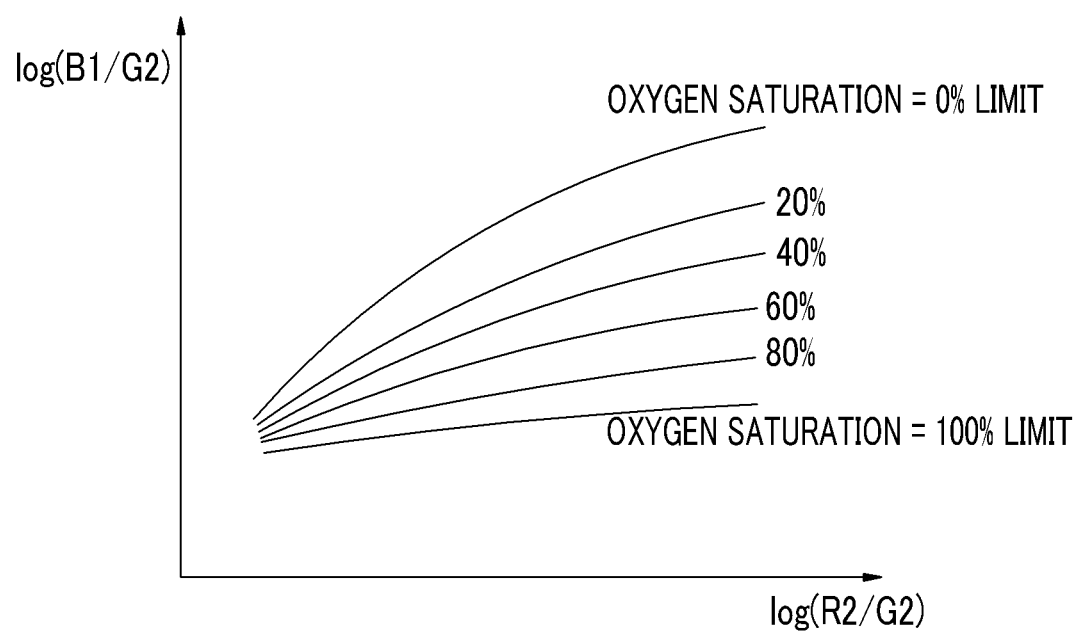
FIG. 8 is a graph showing the correlation between the intensity ratios B1/G2 and R2/G2 and the oxygen saturation.

The correlation storage section 85 stores the correlation between the intensity ratios B1/G2 and R2/G2 and the oxygen saturation. As shown in FIG. 8, this correlation is stored in a two-dimensional table in which the contours of the oxygen saturation on a two-dimensional space are defined. The position and shape of the contour are obtained in a physical simulation of light scattering, and are defined to change according to the blood volume. For example, when there is a change in the blood volume, the distance between the contours increases or decreases. The intensity ratios B1/G2 and R2/G2 are stored in a log scale.

Figure 9:
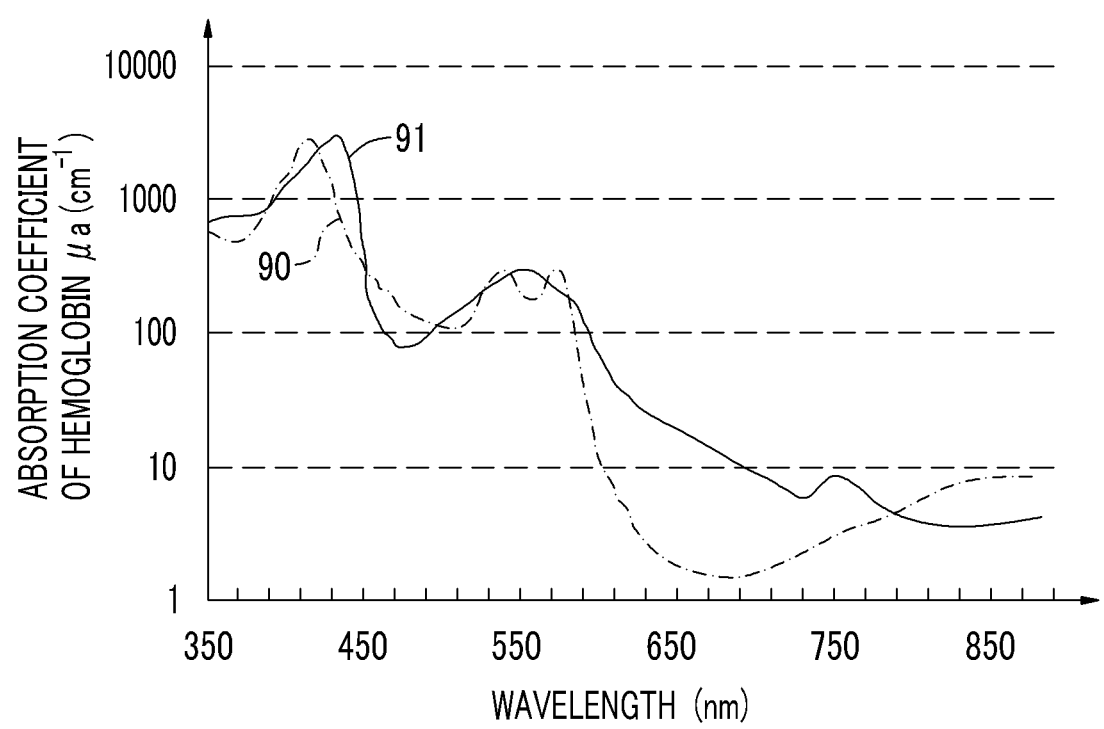
FIG. 9 is a graph showing the absorption coefficients of oxygenated hemoglobin and reduced hemoglobin.

This correlation is closely related to the absorption characteristics or light scattering characteristics of oxygenated hemoglobin or reduced hemoglobin, as shown in FIG. 9. Here, a curve 90 shows the absorption coefficient of oxygenated hemoglobin, and a curve 91 shows the absorption coefficient of reduced hemoglobin. For example, at a wavelength at which the absorption coefficient difference is large, such as 473 nm, it is easy to obtain the information of the oxygen saturation. However, the blue image data B1 including a signal corresponding to 473-nm light has a high dependence not only on the oxygen saturation but also on the blood volume. Therefore, by using the signal ratios B1/G2 and R2/G2 obtained from the blue image data B1, the red image data R2 that changes mainly depending on the blood volume, and the green image data G2 that is a reference signal (normalized signal) of the blue image data B2 and the red image data R2, it is possible to accurately calculate the oxygen saturation without dependence on the blood volume.

Light in the wavelength range of 470 nm to 700 nm has a characteristic that the scattering coefficient in the mucosal tissue is small and the wavelength dependence is small. Therefore, by using the light in this wavelength range as illumination light, it is possible to obtain blood information, including information on the blood volume and oxygen saturation, while reducing the influence of the depth of the blood vessel.

In addition, the correlation between the intensity ratio R2/G2 and the blood volume may also be stored in the correlation storage section 85. This correlation is stored as a one-dimensional table that is defined such that the blood volume increases as the intensity ratio R2/G2 increases. The correlation between the intensity ratio R2/G2 and the blood volume is used when calculating the blood volume.

The oxygen saturation calculation section 86 calculates the oxygen saturation in each pixel using the correlation stored in the correlation storage section 85 and the intensity ratios B1/G2 and R2/G2 calculated by the intensity ratio calculation section 84. In the following explanation, the brightness values of predetermined pixels of the blue image data B1, the green image data G2, and the red image data R2 that are used to calculate the oxygen saturation are assumed to be B1*, G2*, and R2*, respectively. Accordingly, the intensity ratios in respective pixels become B1*/G2* and R2*/G2*.

Figure 10:
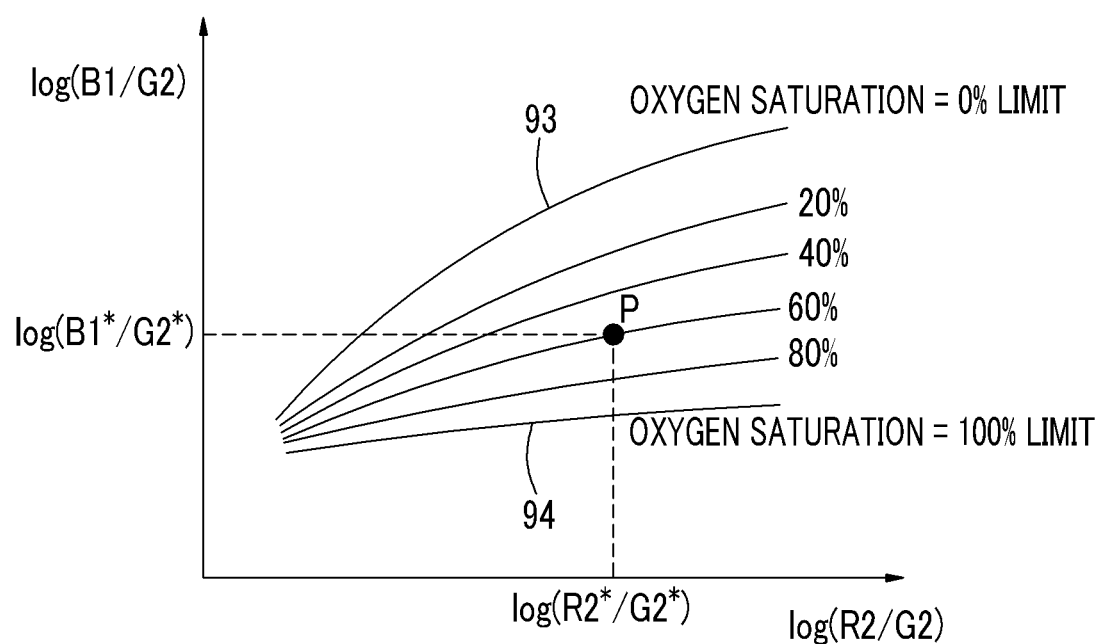
FIG. 10 is a diagram for explaining a method of calculating the oxygen saturation from the correlation shown in FIG. 8.

The oxygen saturation calculation section 86 specifies a corresponding point P that corresponds to the intensity ratios B1*/G2* and R2*/G2* from the correlation stored in the correlation storage section 85, as shown in FIG. 10. When the corresponding point P is between a lower limit line 93 of oxygen saturation=0% limit and an upper limit line 94 of oxygen saturation=100% limit, a percentage value indicated by the corresponding point P is the oxygen saturation. For example, in the case shown in FIG. 10, the oxygen saturation becomes 60% since the corresponding point P is located on the contour of 60%.

On the other hand, when the corresponding point is not located between the lower limit line 93 and the upper limit line 94, the oxygen saturation is 0% when the corresponding point is located above the lower limit line 93, and the oxygen saturation is 100% when the corresponding point is located below the upper limit line 94. When the corresponding point is not located between the lower limit line 93 and the upper limit line 94, the oxygen saturation at the pixel may not be displayed on the display device 14 by lowering the reliability of the oxygen saturation at the pixel.

The oxygen saturation image generation section 87 generates an oxygen saturation image based on the blue signal B2, the green signal G2, and the red signal R2 obtained in the oxygen saturation mode and the oxygen saturation calculated by the oxygen saturation calculation section. Only when the oxygen saturation is less than a predetermined value (for example, 60%), does the oxygen saturation image generation section multiply the blue signal B2 by the gain of "1" or more corresponding to the oxygen saturation, and multiply the green signal G2 and the red signal R2 by the gain of "1" or less corresponding to the oxygen saturation. On the other hand, when the oxygen saturation is equal to or greater than the predetermined value, gain processing is not performed on the blue signal B2, the green signal G2, and the red signal R2.

Figure 11:
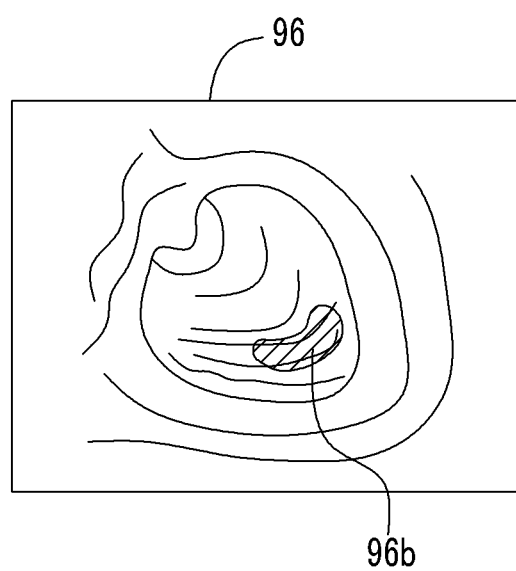
FIG. 11 is an image view showing an oxygen saturation image.

Then, the blue signal B2, the green signal G2, and the red signal R2 after the gain processing are assigned to B, G, and R channels. As a result, as shown in FIG. 11, an oxygen saturation image 96 is displayed on the display device 14. In the oxygen saturation image 96, a portion with a high oxygen saturation is displayed in the same color as a normal image, while a low oxygen region 96a with an oxygen saturation in a certain range (for example, 0% to 60%) set in advance is displayed in blue (that is, the oxygen saturation image 96 becomes an image in which the low oxygen region 96a displayed in pseudo-color, such as blue, is overlap-displayed on the normal image). Instead of displaying only the low oxygen region in pseudo-color as in the oxygen saturation image 96 shown in FIG. 11, the entire oxygen saturation image may be displayed in pseudo-color corresponding to the oxygen saturation.

Figure 12:
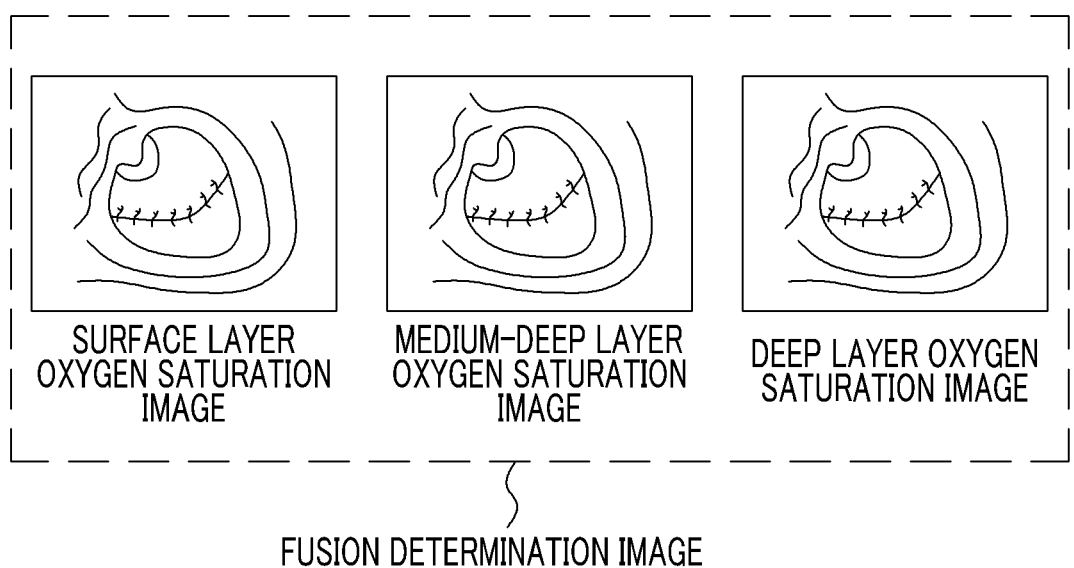
FIG. 12 is an image view showing a fusion determination image.

The fusion determination image processing section 82 generates a fusion determination image, which is used when determining the fusion state of tissues connected together by suturing after tumor resection, based on the image data obtained in the fusion check mode. As shown in FIG. 12, the fusion determination image is configured to include three images of a surface layer oxygen saturation image showing the oxygen state of the surface layer tissue, a medium-deep layer oxygen saturation image showing the oxygen state of the medium-deep layer tissue, and a deep layer oxygen saturation image showing the oxygen state of the deep layer tissue.

Here, the surface layer oxygen saturation image is generated based on the image data Bs, Gs, and Rs. First, the intensity ratio Bs/Gs is obtained by dividing the pixel value of each pixel of the blue image data Bs, which includes information regarding the oxygen saturation of the surface layer tissue, by the pixel value of each pixel of the green image data Gs. Then, gain processing corresponding to the intensity ratio Bs/Gs is performed on the image data Bs, Gs, and Rs of three colors. The surface layer oxygen saturation image in which the low oxygen region of the surface layer tissue is displayed in pseudo-color is obtained from the image data Bs, Gs, and Rs after the gain processing.

The medium-deep layer oxygen saturation image is generated based on the image data Bs, Gs, Rs, and Rt. First, the intensity ratio Rt/Gs is obtained by dividing the pixel value of each pixel of the red image data Rt, which includes information regarding the oxygen saturation of the medium-deep layer tissue, by the pixel value of each pixel of the green image data Gs. Then, gain processing corresponding to the intensity ratio Rt/Gs is performed on the image data Bs, Gs, and Rs of three colors. The medium-deep layer oxygen saturation image in which the low oxygen region of the medium-deep layer tissue is displayed in pseudo-color is obtained from the image data Bs, Gs, and Rs after the gain processing.

The deep layer oxygen saturation image is generated based on the image data Bs, Gs, Rs, and Ru. First, the intensity ratio Ru/Gs is obtained by dividing the pixel value of each pixel of the red image data Ru, which includes information regarding the oxygen saturation of the deep layer tissue, by the pixel value of each pixel of the green image data Gs. Then, gain processing corresponding to the intensity ratio Ru/Gs is performed on the image data Bs, Gs, and Rs of three colors. The deep layer oxygen saturation image in which the low oxygen region of the deep layer tissue is displayed in pseudo-color is obtained from the image data Bs, Gs, and Rs after the gain processing.

Figure 13A:
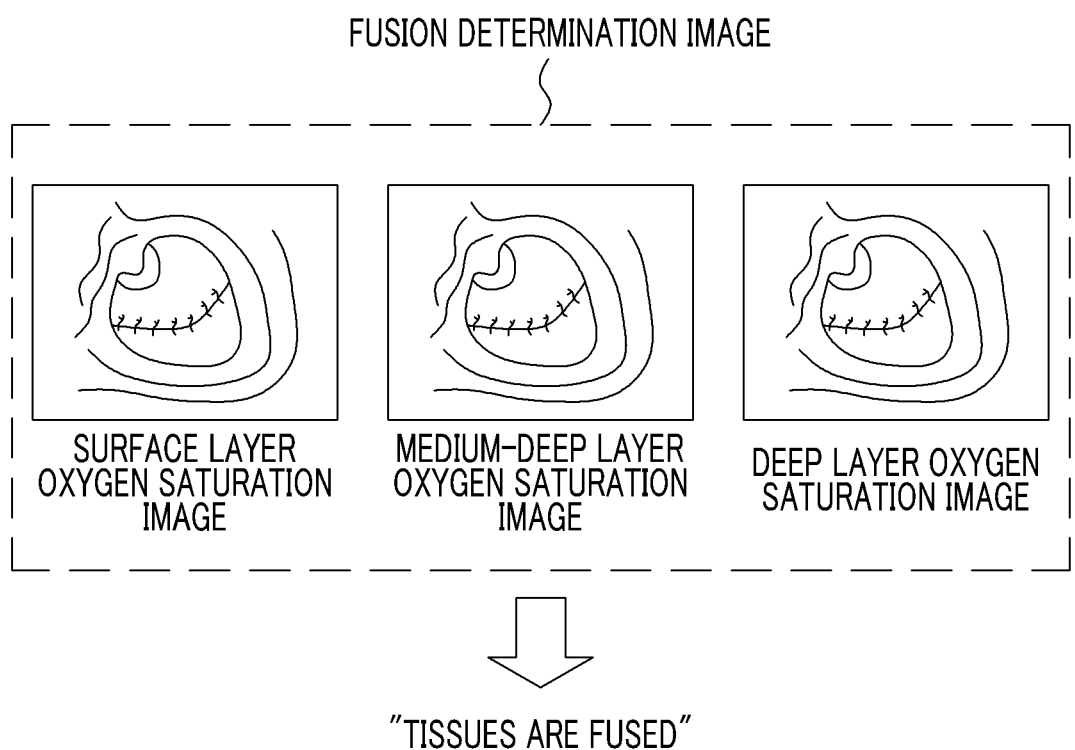
FIG. 13A is an image view showing a fusion determination image when tissues are fused.
Figure 13B:
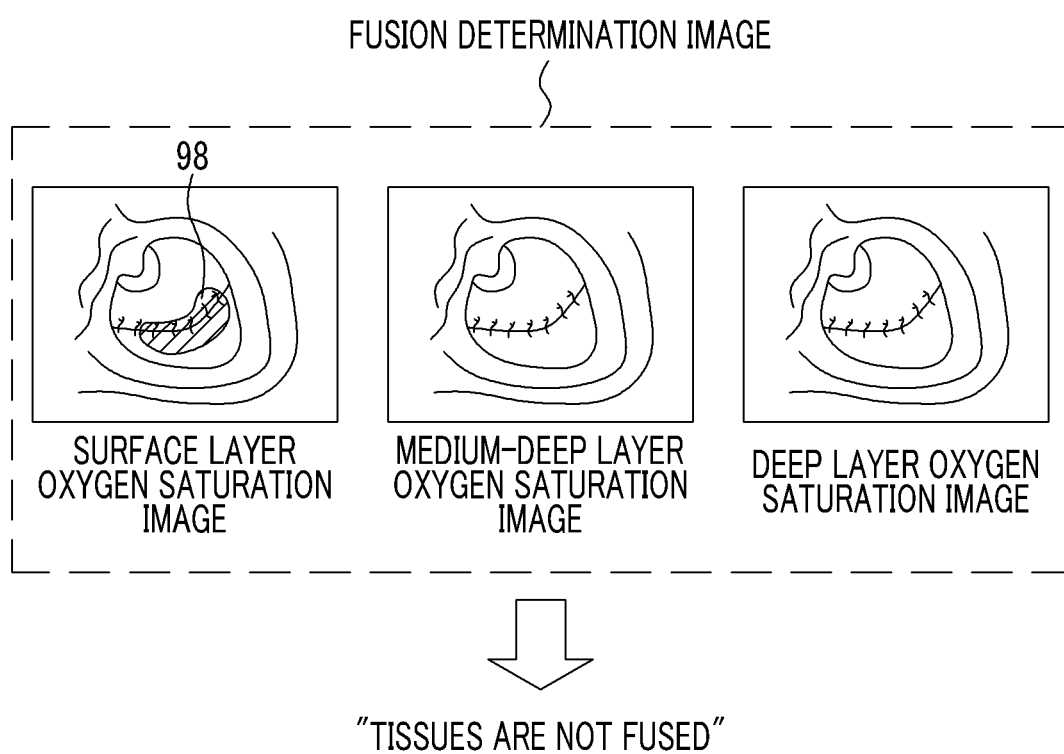
FIG. 13B is an image view showing a fusion determination image when tissues are not fused.

As shown in FIG. 13A, when there is no low oxygen region in the surface layer oxygen saturation image, the medium-deep layer oxygen saturation image, and the deep layer oxygen saturation image, it is thought that the tissues connected together by suturing are fused. In this case, there is no need of re-suturing. On the other hand, as shown in FIG. 13B, when there is a low oxygen region 98 in any of the surface layer oxygen saturation image, the medium-deep layer oxygen saturation image, and the deep layer oxygen saturation image, it is thought that the tissues have not been fused. In this case, re-suturing between tissues is considered.

The suture state determination section 83 performs processing when the automatic determination mode is set, and determines the suture state of tissues connected together by suturing based on the oxygen saturation image obtained in the oxygen saturation mode. The suture state determination section 83 detects the area of the low oxygen region 96a, which has an oxygen saturation in a certain range (for example, 0% to 60%) set in advance, in the oxygen saturation image 96. When the area of the low oxygen region 96a is equal to or greater than a predetermined value, it is determined that there is suture failure since the tissues connected together by suturing have not been fused. In this case, the display of "there is a possibility of suture failure" is displayed on the display device 14. On the other hand, when the area of the low oxygen region 96a is less than the predetermined value, it is determined that there is no suture failure since the tissues are fused. In this case, the display of "suture state is good" is displayed on the display device 14.

The suture state determination section 83 may determine the suture state based on the oxygen saturation images of three layers that are the surface layer oxygen saturation image, the medium-deep layer oxygen saturation image, and the deep layer oxygen saturation image obtained in the fusion check mode. In this case, as a method for determining the suture state, various methods can be considered. For example, it is determined that "there is a possibility of suture failure" when the area of a low oxygen region is equal to or greater than the predetermined value in two or more of the oxygen saturation images of the three layers, and it is determined that "there is no suture state" when the area of a low oxygen region is equal to or greater than the predetermined value in one of the oxygen saturation images of the three layers or when there is no oxygen saturation image in which the area of a low oxygen region is equal to or greater than the predetermined value. These determination results are displayed on the display device 14.

Figure 14:
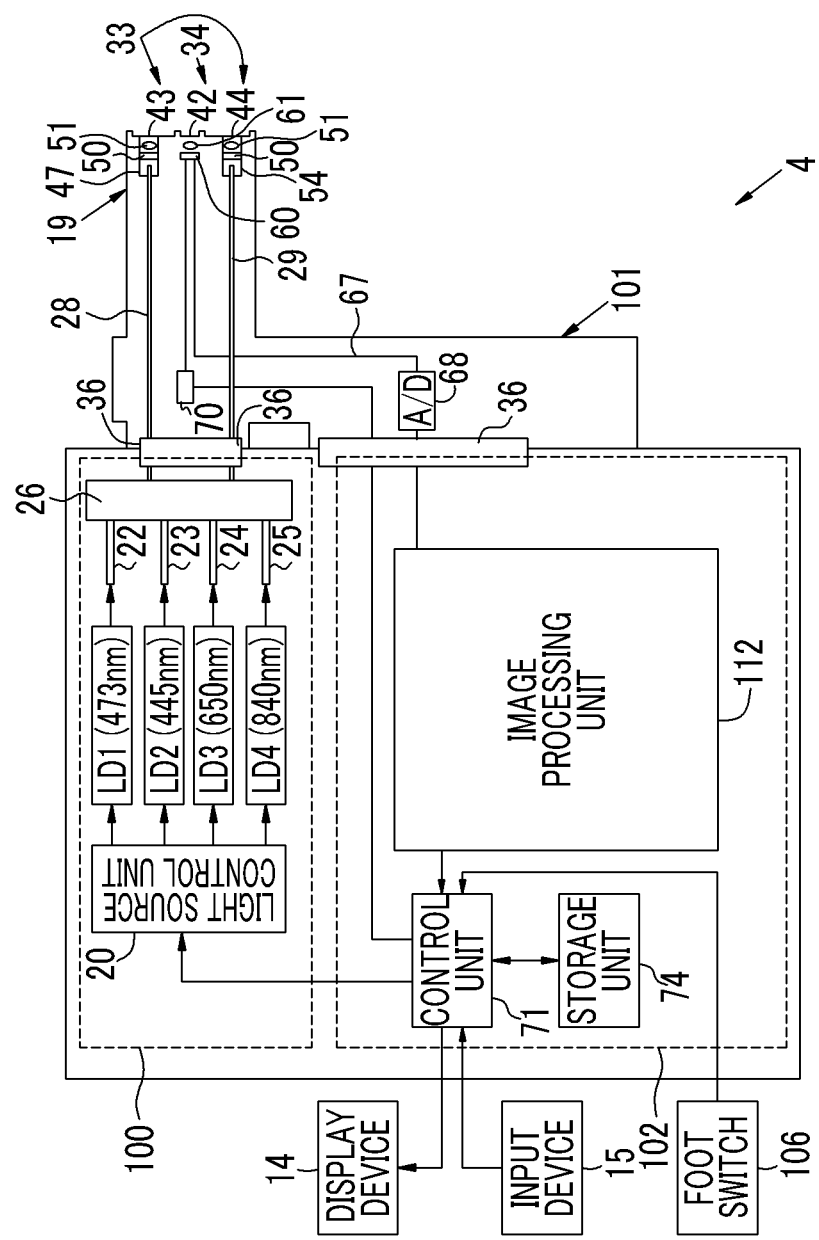
FIG. 14 is a block diagram of an abdominal cavity endoscope system.

As shown in FIG. 14, the internal configuration of the abdominal cavity endoscope system 4 is approximately the same as that of the luminal cavity endoscope system shown in FIG. 3 except for the light source control of the laser light sources LD1 to LD4, the imaging control of the imaging device 60, and the internal configuration of an image processing unit 112. Regarding the light source control of the laser light sources LD1 to LD4, light source control in the normal mode and the oxygen saturation mode is the same as the light source control of the luminal cavity light source device 11. On the other hand, for the light source control in the infiltration check mode, light source control to sequentially emit the first to third oxygen saturation measurement light beams in the infiltration measuring step is performed (refer to FIG. 4C).

In addition, regarding the imaging control of the imaging device 60, imaging control in the normal mode and the oxygen saturation mode is the same as the imaging control of the luminal cavity endoscope apparatus 12. On the other hand, for the imaging control in the infiltration check mode, imaging control to sequentially capture a reflected image of the subject illuminated with the first oxygen saturation measurement light, a reflected image of the subject illuminated with the second oxygen saturation measurement light, and a reflected image of the subject illuminated with the third oxygen saturation measurement light is performed (refer to FIG. 6C). By imaging of the subject in the infiltration check mode, nine pieces of image data Bs, Gs, Rs, Bt, Gt, Rt, Bu, Gu, and Ru are obtained.

Figure 15:
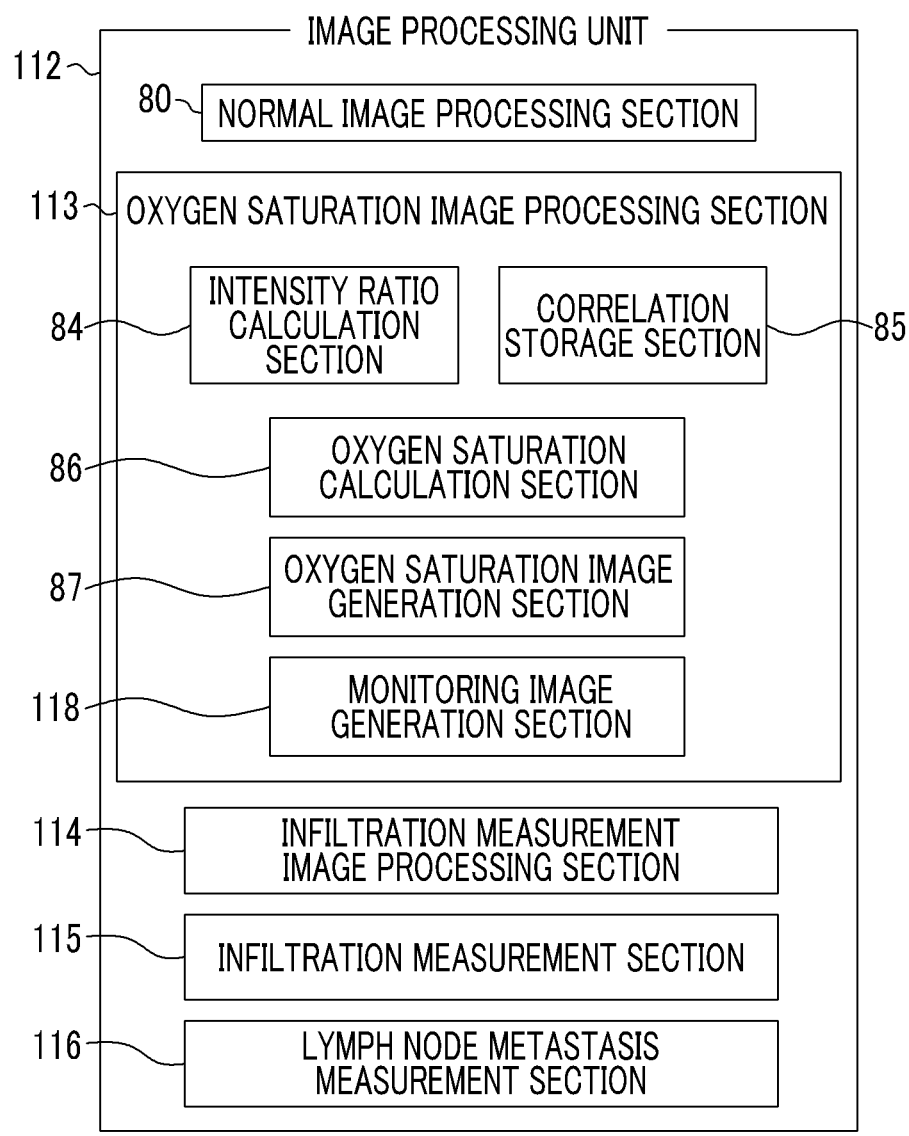
FIG. 15 is a block diagram showing an image processing unit in an abdominal cavity processor device.

As shown in FIG. 15, the image processing unit 112 includes a normal image processing section 80, an oxygen saturation image processing section 113, an infiltration measurement image processing section 114, an infiltration measurement section 115, and a lymph node metastasis measurement section 116. The normal image processing section 80 is the same as the normal image processing section 80 of the luminal cavity processor device 13. The oxygen saturation image processing section 113 includes a monitoring image generation section 118 in addition to the sections 84 to 87 of the oxygen saturation image processing section 81 of the luminal cavity processor device 12.

Figure 16:
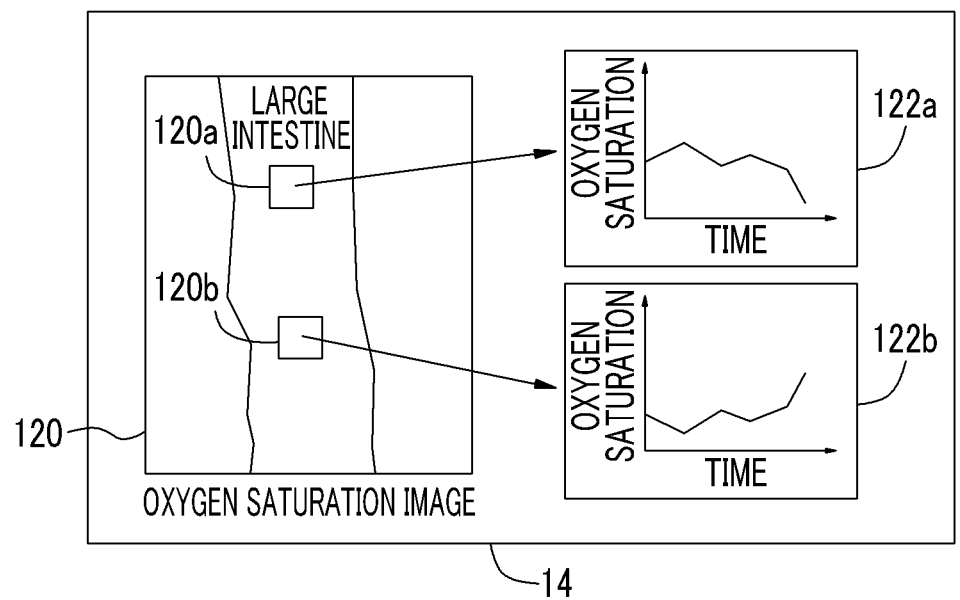
FIG. 16 is an image view showing a monitoring image.

As shown in FIG. 16, the monitoring image generation section 118 generates a monitoring image configured to include an oxygen saturation image 120 and graphs 122a and 122b that are located next to the oxygen saturation image and show the oxygen saturation of a plurality of regions of interest 120a and 120b over time. As the oxygen saturation of each of the regions of interest 122a and 122b, the oxygen saturation calculated by the oxygen saturation calculation section 86 is used. The calculated oxygen saturation is plotted on the graphs 122a and 122b whenever the oxygen saturation image 120 is updated. In addition, the setting of a region of interest is performed by using the input device 15.

Figure 17:
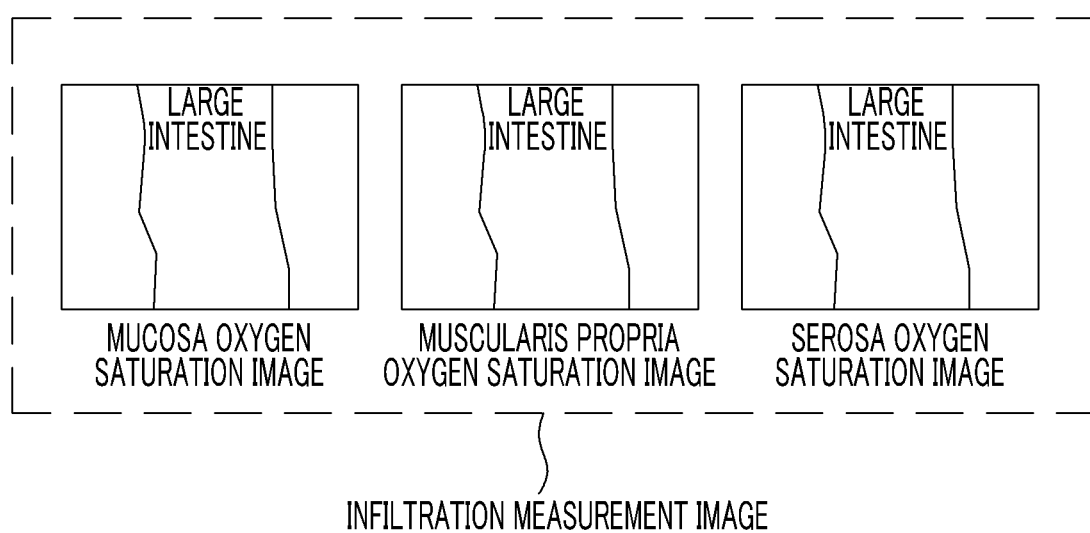
FIG. 17 is an image view of an infiltration measurement image.

As shown in FIG. 17, the infiltration measurement image processing section 114 generates an infiltration measurement image, which is used when measuring the extent of infiltration of a tumor within the tissue, based on the image data obtained in the fusion check mode. The infiltration measurement image is configured to include three images of a mucosa oxygen saturation image showing the oxygen state in the vicinity of the mucosa of the large intestine, a muscularis propria oxygen saturation image showing the oxygen state in the vicinity of the muscularis propria of the large intestine, and a serosa oxygen saturation image showing the oxygen state in the vicinity of the serosa of the large intestine.

Here, the mucosa oxygen saturation image is generated based on the image data Bs, Gs, Rs, and Ru. First, the intensity ratio Ru/Gs is obtained by dividing the pixel value of each pixel of the red image data Ru, which includes information regarding the oxygen saturation of the mucosal tissue, by the pixel value of each pixel of the green image data Gs. Then, gain processing corresponding to the intensity ratio Ru/Gs is performed on the image data Bs, Gs, and Rs of three colors. The mucosa oxygen saturation image in which the low oxygen region of the mucosal tissue is displayed in pseudo-color is obtained from the image data Bs, Gs, and Rs after the gain processing.

The muscularis propria oxygen saturation image is generated based on the image data Bs, Gs, Rs, and Rt. First, the intensity ratio Rt/Gs is obtained by dividing the pixel value of each pixel of the red image data Rt, which includes information regarding the oxygen saturation of the muscularis propria, by the pixel value of each pixel of the green image data Gs. Then, gain processing corresponding to the intensity ratio Rt/Gs is performed on the image data Bs, Gs, and Rs of three colors. The medium-deep layer oxygen saturation image in which the low oxygen region of the muscularis propria is displayed in pseudo-color is obtained from the image data Bs, Gs, and Rs after the gain processing.

The serosa oxygen saturation image is generated based on the image data Bs, Gs, and Rs. First, the intensity ratio Bs/Gs is obtained by dividing the pixel value of each pixel of the blue image data Bs, which includes information regarding the oxygen saturation in the vicinity of the serosa, by the pixel value of each pixel of the green image data Gs. Then, gain processing corresponding to the intensity ratio Bs/Gs is performed on the image data Bs, Gs, and Rs of three colors. The deep layer oxygen saturation image in which the low oxygen region near the serosa is displayed in pseudo-color is obtained from the image data Bs, Gs, and Rs after the gain processing.

Figure 18A:
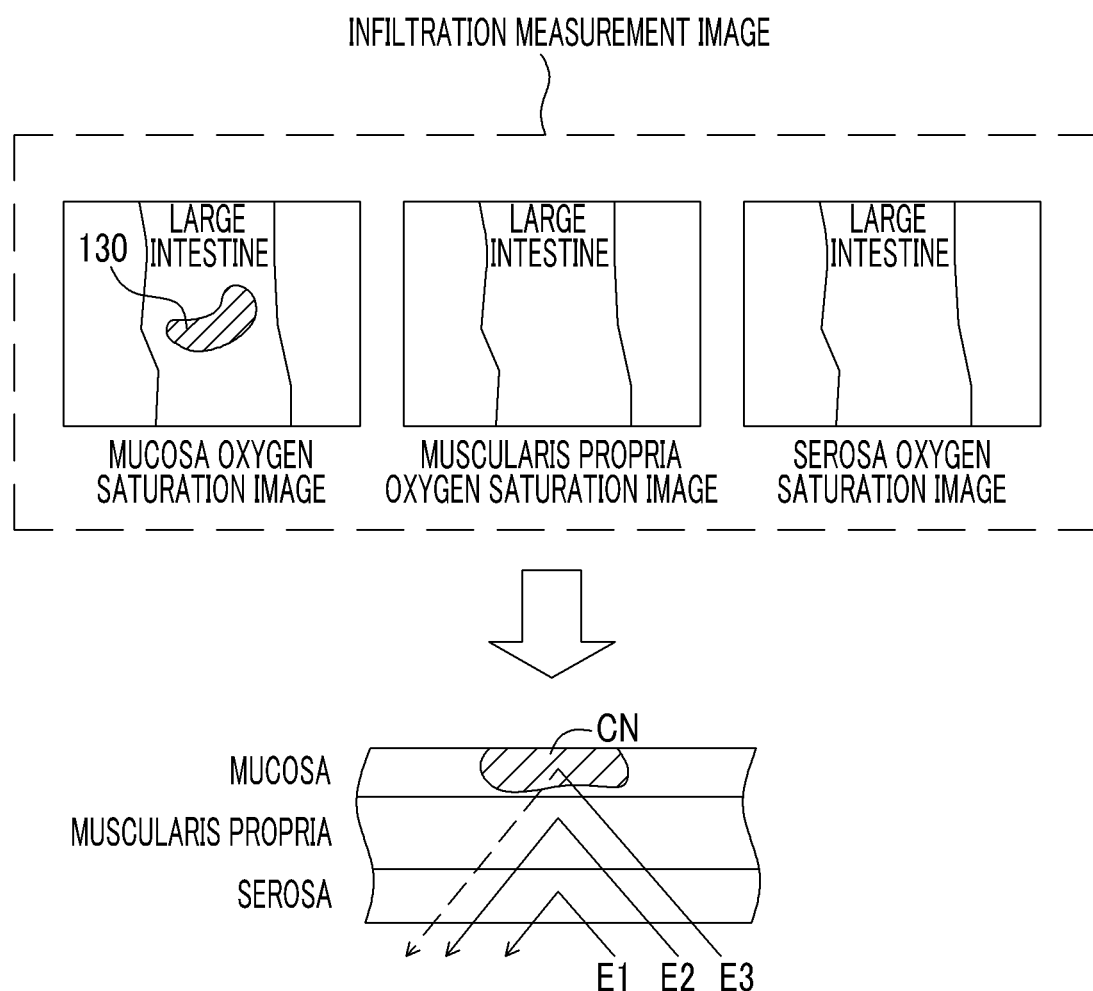
FIG. 18A is an image view of an infiltration measurement image when a tumor has infiltrated the mucosa.

As shown in FIG. 18A, when a low oxygen region 130 is displayed only in the mucosa oxygen saturation image and no low oxygen region is displayed in the muscularis propria oxygen saturation image and the serosa oxygen saturation image, third oxygen saturation measurement light E3 reaching deep down to the mucosa from the abdominal cavity side contributes to the detection of a tumor CN, but first and second oxygen saturation measurement light beams E1 and E2 reaching deep down to the muscularis propria and the serosa do not contribute to the detection of the tumor CN. In this case, the operator determines that the measured part is "T1" indicating that the tumor has infiltrated only to the vicinity of the mucosa using a measurement unit 114b. Here, the low oxygen region in each of the mucosa oxygen saturation image and the serosa oxygen saturation image is a region where the intensity ratios Ru/Gs and Bs/Gs exceed a predetermined value, and the low oxygen region in the muscularis propria oxygen saturation image is a region where the intensity ratio Rt/Gs is less than the predetermined value.

Figure 18B:
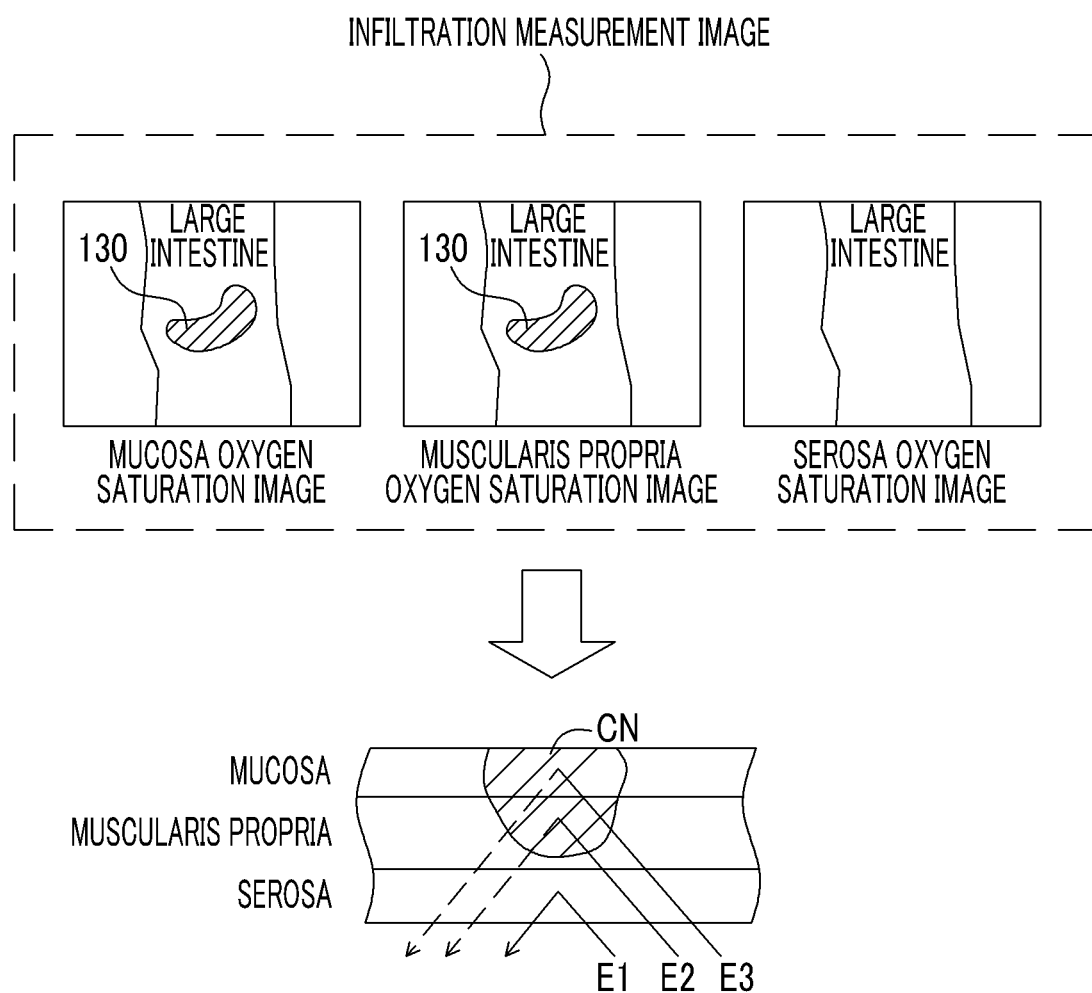
FIG. 18B is an image view of an infiltration measurement image when a tumor has infiltrated the muscularis propria.

In addition, as shown in FIG. 18B, when the low oxygen region 130 is displayed in the mucosa oxygen saturation image and the muscularis propria oxygen saturation image and no low oxygen region is displayed in the serosa oxygen saturation image, the second and third oxygen saturation measurement light beams E2 and E3 contribute to the detection of the tumor CN, but the first oxygen saturation measurement light E1 does not contribute to the detection of the tumor CN. In this case, the operator determines that the measured part is "T2" or "T3" indicating that the tumor has infiltrated to the vicinity of the muscularis propria.

Figure 18C:
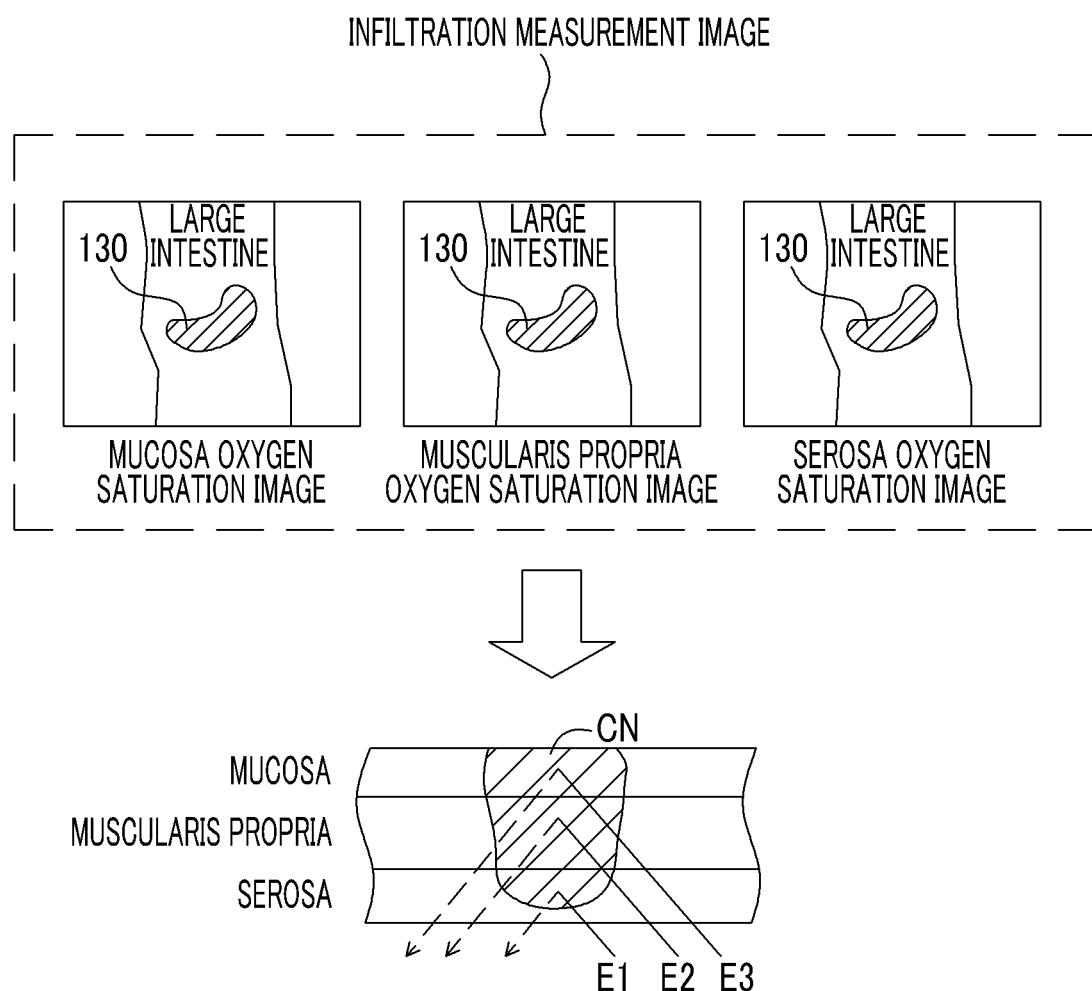
FIG. 18C is an image view of an infiltration measurement image when a tumor has infiltrated the serosa.

In addition, as shown in FIG. 18C, when the low oxygen region 130 is displayed in all of the mucosa oxygen saturation image, the muscularis propria oxygen saturation image, and the serosa oxygen saturation image, all of the first to third oxygen saturation measurement light beams E1, E2 and E3 contribute to the detection of the tumor CN. In this case, the operator determines that the measured part is "T4" indicating that the tumor has infiltrated to the vicinity of the serosa.

The infiltration measurement section 115 performs processing when the automatic determination mode is set, and automatically measures the extent of infiltration based on the three oxygen saturation images including the mucosa oxygen saturation image, the muscularis propria oxygen saturation image, and the serosa oxygen saturation image obtained in the infiltration measurement mode. First, the infiltration measurement section 115 detects a low oxygen region in each of the three oxygen saturation images. Here, the low oxygen region in each of the mucosa oxygen saturation image and the serosa oxygen saturation image is a region where the intensity ratios Ru/Gs and Bs/Gs exceed a predetermined value, and the low oxygen region in the muscularis propria oxygen saturation image is a region where the intensity ratio Rt/Gs is less than the predetermined value.

The infiltration measurement section 115 performs determination as "T1" when the low oxygen region is detected only in the mucosa oxygen saturation image, performs determination as "T2" or "T3" when the low oxygen region is detected in the mucosa oxygen saturation image and the muscularis propria oxygen saturation image, and performs determination as "T4" when the low oxygen region is detected in all of the mucosa oxygen saturation image, the muscularis propria oxygen saturation image, and the serosa oxygen saturation image. The determination result is displayed on the display device 14.

Figure 19A:
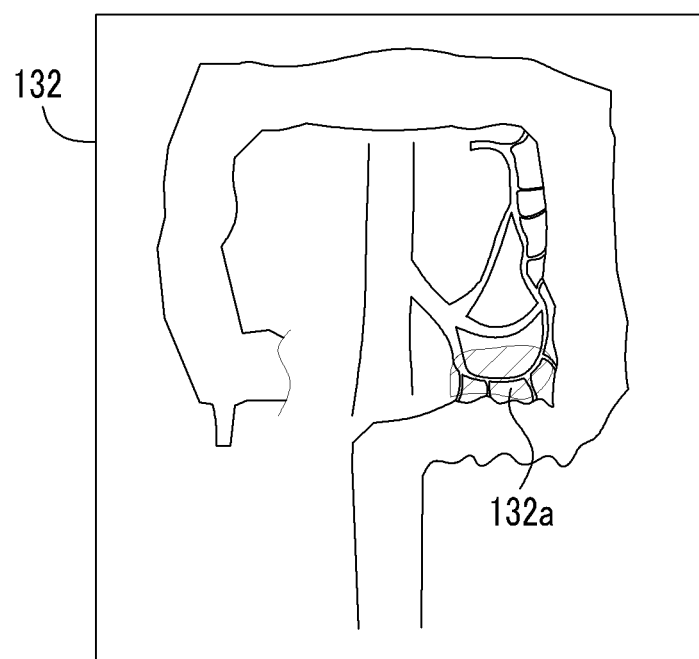
FIG. 19A is an image view of an oxygen saturation image when metastasis to lymph nodes is "N0".
Figure 19B:
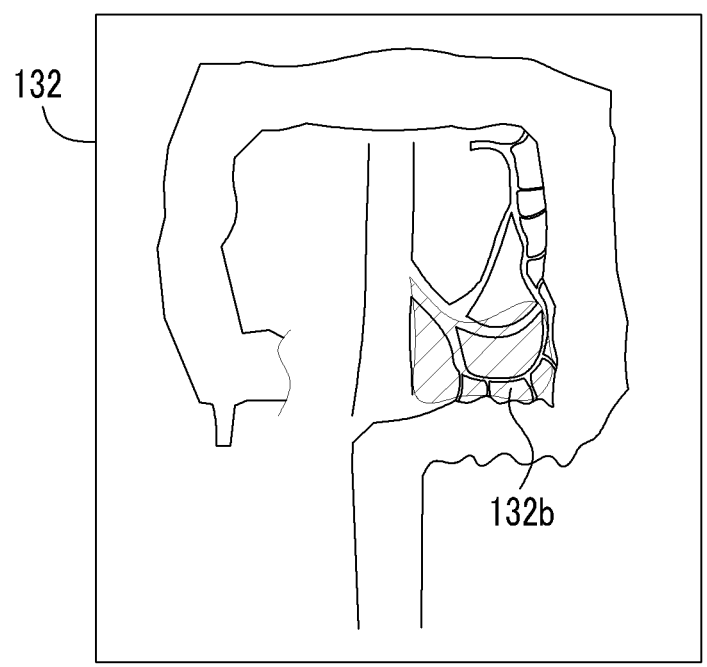
FIG. 19B is an image view of an oxygen saturation image when the metastasis to lymph nodes is "N1".
Figure 19C:
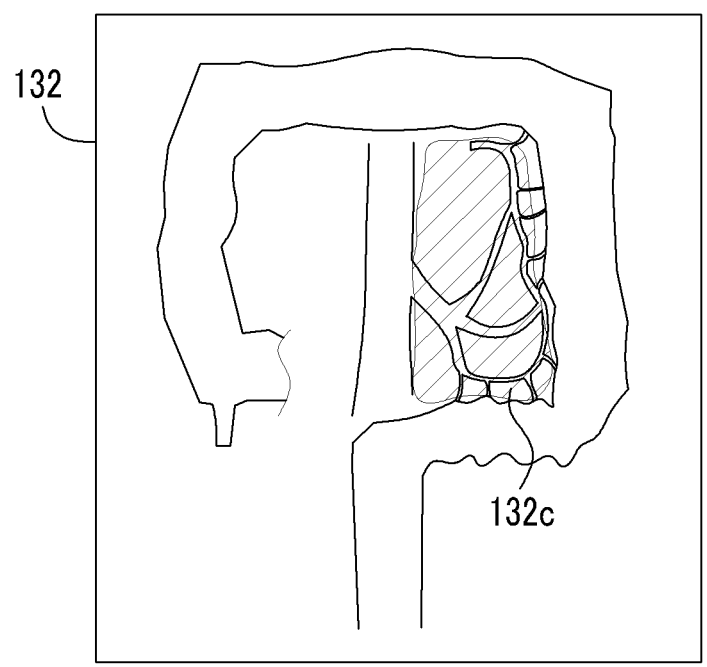
FIG. 19C is an image view of an oxygen saturation image when the metastasis to lymph nodes is "N2".

In addition, in the abdominal cavity endoscope system 4, it is possible to measure the extent of metastasis to lymph nodes traveling in parallel with the arterial blood vessels and the like in the oxygen saturation mode. For example, if the size of a low oxygen region 132a in an oxygen saturation image 132 is equal to or less than S1 set in advance as shown in FIG. 19A, metastasis to lymph nodes can be determined as "N0". In addition, if the size of a low oxygen region 132b is within the range of S1 to S2 (S1<S2) as shown in FIG. 19B, metastasis to lymph nodes can be determined as "N1". In addition, if the size of a low oxygen region 132c is larger than S2 as shown in FIG. 19C, metastasis to lymph nodes can be determined as "N2".

The metastasis to the lymph nodes can also be automatically determined by the lymph node metastasis measurement section 116. The lymph node metastasis measurement section 116 performs processing when the automatic determination mode is set, and automatically measures the extent of lymph node metastasis based on the oxygen saturation image obtained in the oxygen saturation mode. The lymph node metastasis measurement section 116 detects the size of a low oxygen region, which has oxygen saturation in a certain range (for example, 0% to 60%) set in advance, in the oxygen saturation image 132. The lymph node metastasis measurement section 116 performs determination as "N0" if the size of the low oxygen region is equal to or less than S1 (refer to FIG. 19A), performs determination as "N1" if the size of the low oxygen region is within the range of S1 to S2 (refer to FIG. 19B), and performs determination as "NT" if the size of the low oxygen region is larger than S2 (refer to FIG. 19C). These determination results are displayed on the display device 14.

Figure 20:
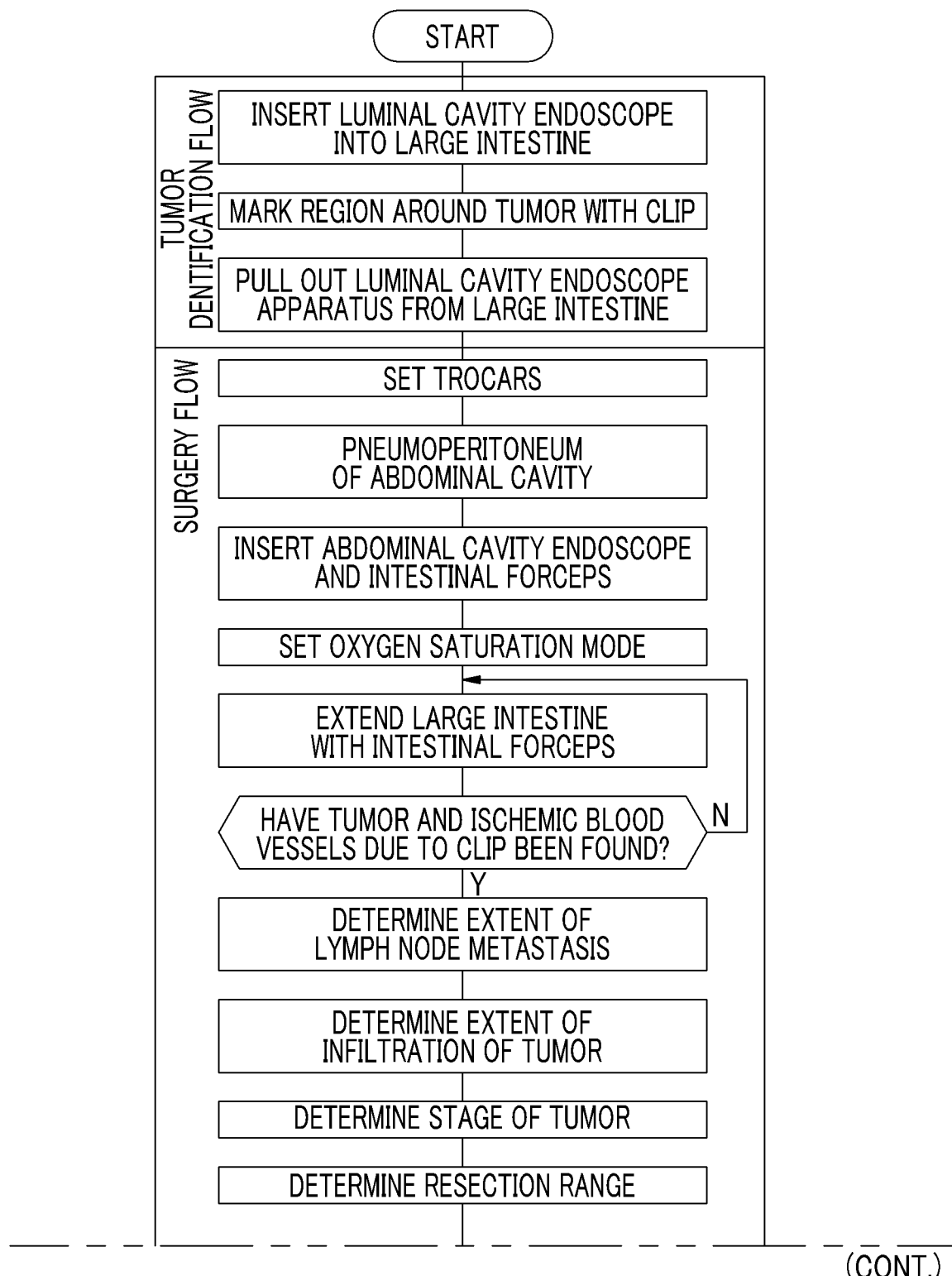
FIG. 20 is a flowchart showing the tumor identification flow, the surgery flow, and the fusion check flow.

Next, large intestine resection using the luminal cavity endoscope system 3 and the abdominal cavity endoscope system 4 will be described. As shown in FIG. 20, the large intestine resection process is divided into three flows including a tumor identification flow for identifying the location of a tumor using the luminal cavity endoscope system 3 before surgery, a surgery flow for resecting the tumor using the abdominal cavity endoscope system 4, and a fusion check flow for checking the fusion between tissues connected together by suturing using the abdominal cavity endoscope system 4 after surgery.

Figure 21:
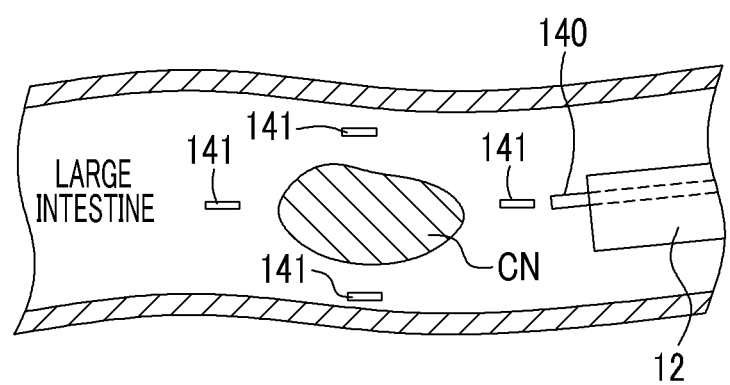
FIG. 21 is a cross-sectional view of the large intestine to which a clip is attached.

First, in the tumor identification flow, the normal mode is set, and the luminal cavity endoscope apparatus 12 is inserted into the large intestine through the anus. Then, a normal image in the large intestine from the luminal side is displayed on the display device 14. The operator locates a part with a tumor while observing the normal image in the lumen displayed on the display device 14. Once the tumor CN is found, the operator inserts a clip device 140 through the forceps channel 20, as shown in FIG. 21. Then, the operator presses a relatively thick blood vessel near the tumor CN with a clip 141 by operating the clip device 140. The tissue around the blood vessel that has been pressed by the clip 141 becomes ischemic, and accordingly, becomes a low oxygen region where the blood oxygen saturation has been reduced. This low oxygen region serves as a mark when identifying the tumor in the next surgery flow. After putting a mark with the clip 141, the luminal cavity endoscope apparatus 12 is pulled out from the large intestine.

Figure 22:
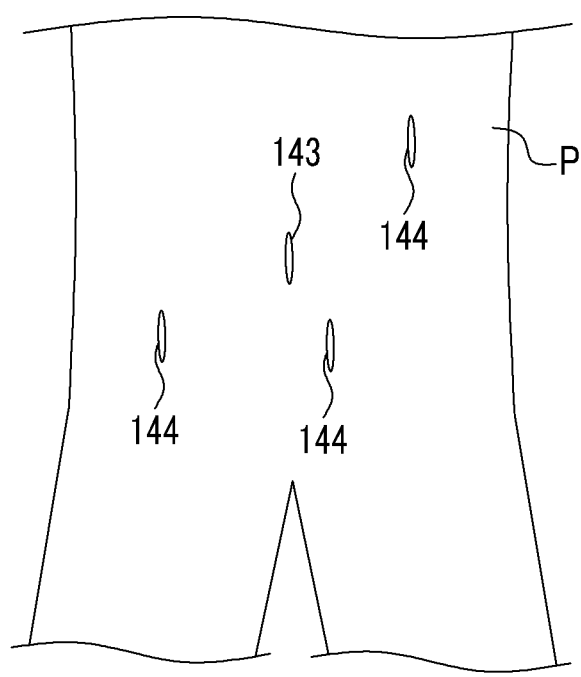
FIG. 22 is a plan view showing the abdomen of a patient having a hole for scopes and a hole for treatment tools that are opened.

In the surgery flow, first, as shown in FIG. 22, a hole 143 for scopes is opened at a position, at which the abdominal cavity endoscope apparatus 101 is inserted, on the abdomen of the patient, and a plurality of holes 144 for treatment tools are opened at positions, at which various treatment tools, such as intestinal forceps, a hemostatic probe electric scalpel, and an automatic suturing device. Then, the trocar 110 is pierced through the hole 143 for scopes, and the trocar 109 is pierced through the holes 144 for treatment tools (refer to FIG. 2). Then, the abdominal cavity endoscope apparatus 101 and various treatment tools are inserted to the trocars 110 and 109. Thereafter, pneumoperitoneum gas is supplied into the abdominal cavity by the pneumoperitoneum device 107. Therefore, since pneumoperitoneum of the abdominal cavity is performed, it is possible to ensure the field of view for surgery in the abdominal cavity.

Figure 23:
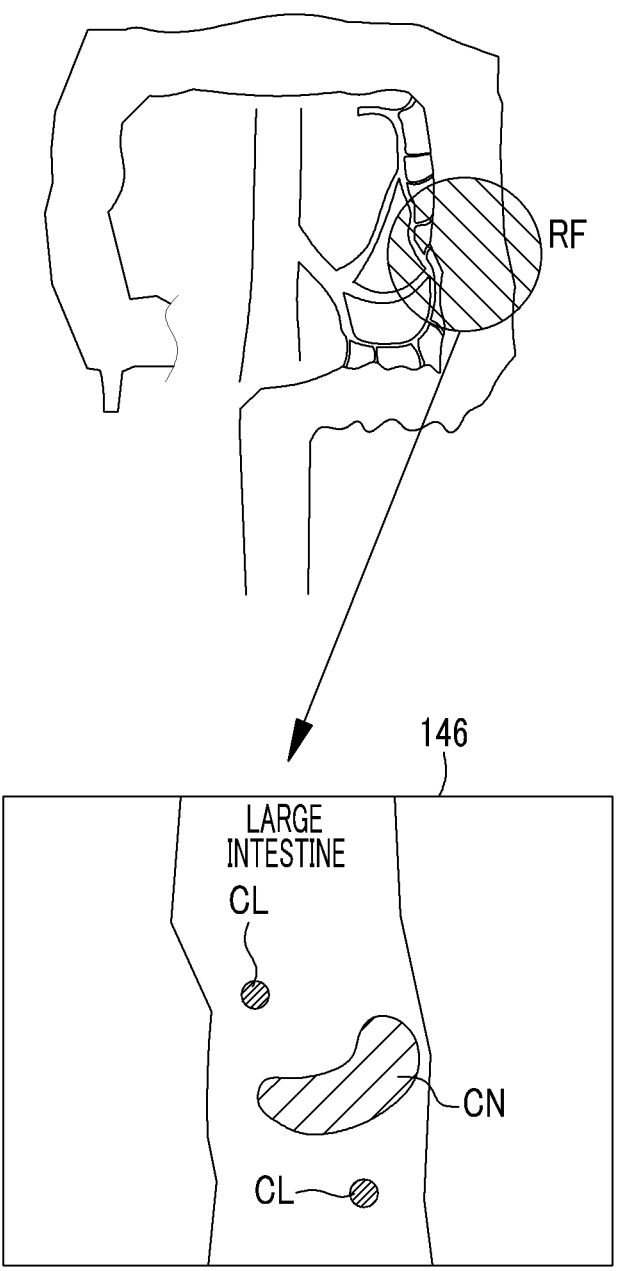
FIG. 23 is a plan view of the large intestine illuminated with light from the abdominal cavity side and an image view showing an oxygen saturation image of the large intestine of the illuminated portion.

Then, the oxygen saturation mode is set, and the first oxygen saturation measurement light and the normal light are alternately emitted from the abdominal cavity side and a reflected image RF illuminated with these light beams is captured, as shown in FIG. 23. As a result, an oxygen saturation image 146 from the abdominal cavity side is displayed on the display device 14. By observing the oxygen saturation image 146, the operator locates the tumor CN in a low oxygen state, and locates an ischemic portion CL that has changed into the low oxygen state by the clip 141 as a mark of the tumor before surgery.

Figure 24:
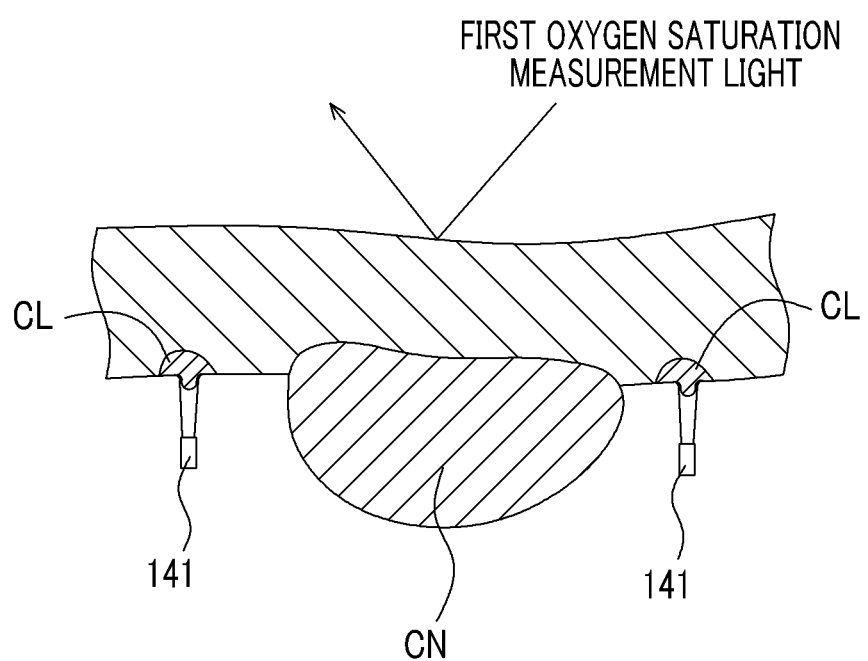
FIG. 24 is a cross-sectional view of the large intestine showing a tumor CN and an ischemic portion that has fallen into the low oxygen state by a clip.

Here, the center wavelength of the first oxygen saturation measurement light used to generate the oxygen saturation image 146 is 460 nm to 480 nm in a short wavelength band. Therefore, as shown in FIG. 24, the first oxygen saturation measurement light may not reach deep down to the tumor CN or the ischemic portion CL. In this case, the tumor CN or the ischemic portion CL may not be displayed as low oxygen regions on the oxygen saturation image 146 even though the tumor CN or the ischemic portion CL is being imaged.

Figure 25:
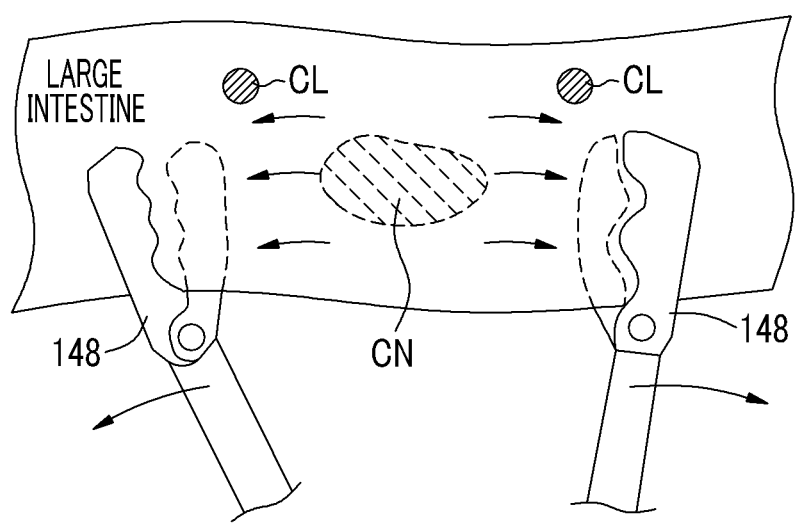
FIG. 25 is a plan view of the large intestine in a state where the serosa is extended by the intestinal forceps.
Figure 26:
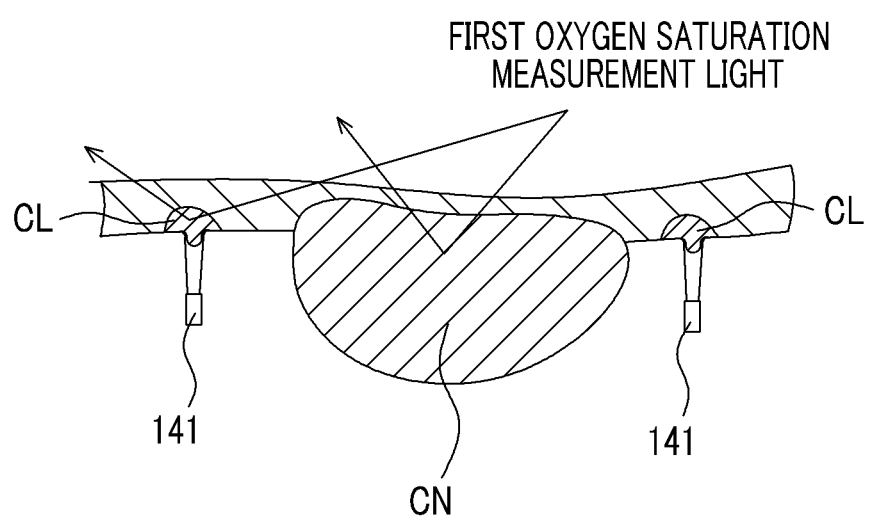
FIG. 26 is a cross-sectional view of the large intestine in a state where the serosa is extended by the intestinal forceps.

Therefore, as shown in FIG. 25, a part assumed to be the tumor CN is extended using intestinal forceps. As a result, since the thickness of the serosa of the large intestine is reduced, the first oxygen saturation measurement light and the normal light surely reach deep down to the tumor CN and the ischemic portion CL, as shown in FIG. 26. Therefore, on the oxygen saturation image 146, the tumor CN or the ischemic portion CN is clearly displayed as a low oxygen region.

After identifying the location of the tumor CN in the oxygen saturation image 146, an oxygen saturation image in which the tumor of the large intestine and the arterial blood vessel or the venous blood vessel around the tumor have been projected is displayed on the display device 14 by expanding the imaging field of view. Then, the oxygen state of the arterial blood vessel or the venous blood vessel in the oxygen saturation image is checked. From the oxygen state of the arterial blood vessels or the venous blood vessels, it is possible to check whether or not there is metastasis of cancer to the lymph nodes traveling in parallel with the arterial blood vessels. That is, the operator can determine the extent ("N0", "N1", or "N2") of metastasis to lymph nodes from the oxygen state of the arterial blood vessel.

Figure 27A:
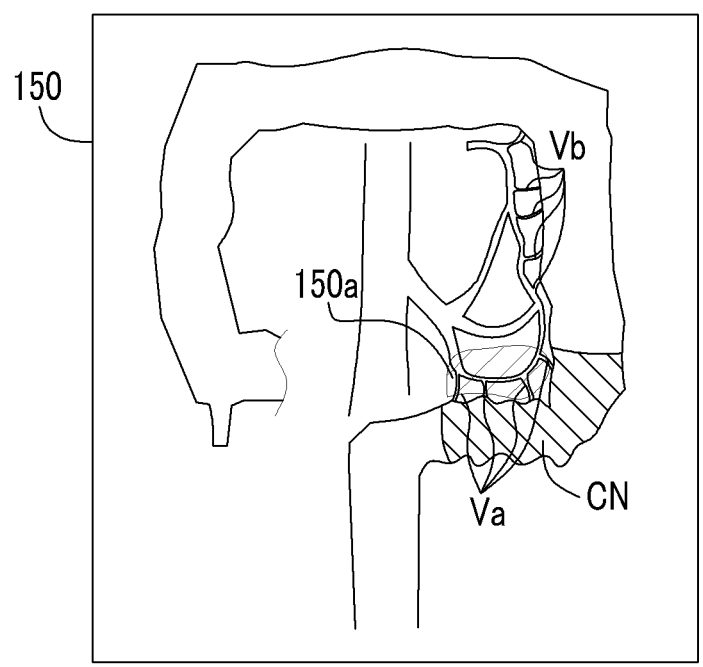
FIG. 27A is an image view of an oxygen saturation image when cancer has metastasized only to lymph nodes around the tumor CN.

As shown in FIG. 27A, in the oxygen saturation image 150, when only the surrounding tissue of an arterial blood vessel Va connected to the tumor CN is displayed as a low oxygen region 150a and the surrounding tissue of an arterial blood vessel Vb connected to a part other than the tumor CN is displayed as a high oxygen region, the operator determines that cancer has metastasized only to lymph nodes connected to the tumor CN and there is no metastasis of cancer to lymph nodes connected to a part other than the tumor CN.

Figure 27B:
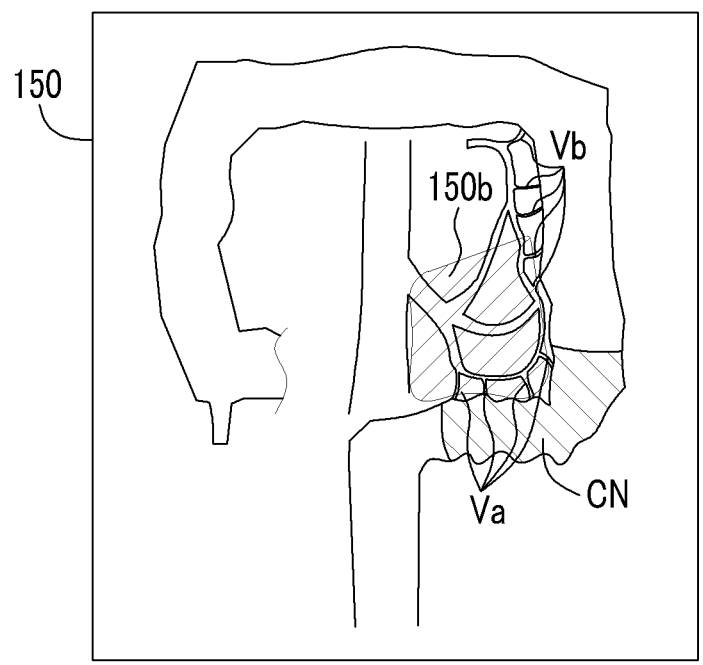
FIG. 27B is an image view of an oxygen saturation image when cancer has metastasized to lymph nodes around the tumor CN and lymph nodes around the normal part.

On the other hand, as shown in FIG. 27B, when not only the surrounding tissue of the arterial blood vessel Va connected to the tumor but also the surrounding tissue of the arterial blood vessel Vb connected to a part other than the tumor is displayed as a low oxygen region 150b, the operator determines that cancer has metastasized not only to lymph nodes connected to the tumor CN but also to lymph nodes connected to a part other than the tumor CN. That is, the operator determines that there is a possibility that the cancer has metastasized not only to the tumor CN but also to other parts.

After checking the lymph node metastasis from the oxygen saturation image, the abdominal cavity endoscope apparatus 101 is operated again so that the imaging field of view is moved toward the tumor and the surrounding region. Then, switching to the infiltration check mode is performed. By this mode switching, three images including the mucosa oxygen saturation image, the muscularis propria oxygen saturation image, and the serosa oxygen saturation image are displayed in parallel on the display device 14 (refer to FIG. 17). The operator determines the extent of infiltration of cancer subjectively from the three oxygen saturation images.

Figure 28A:
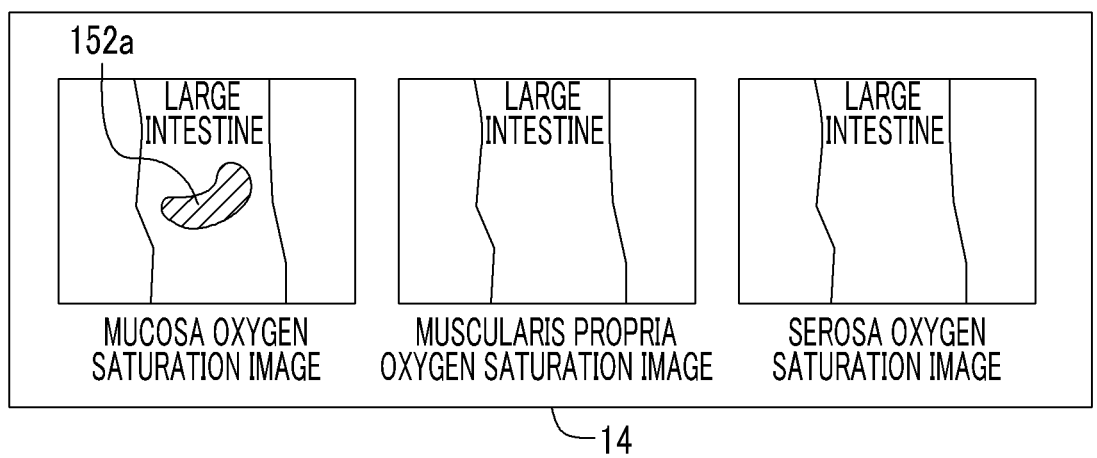
FIG. 28A is an image view showing a mucosa oxygen saturation image, a muscularis propria oxygen saturation image, and a serosa oxygen saturation image when the infiltration of the tumor is "T1".
Figure 28B:
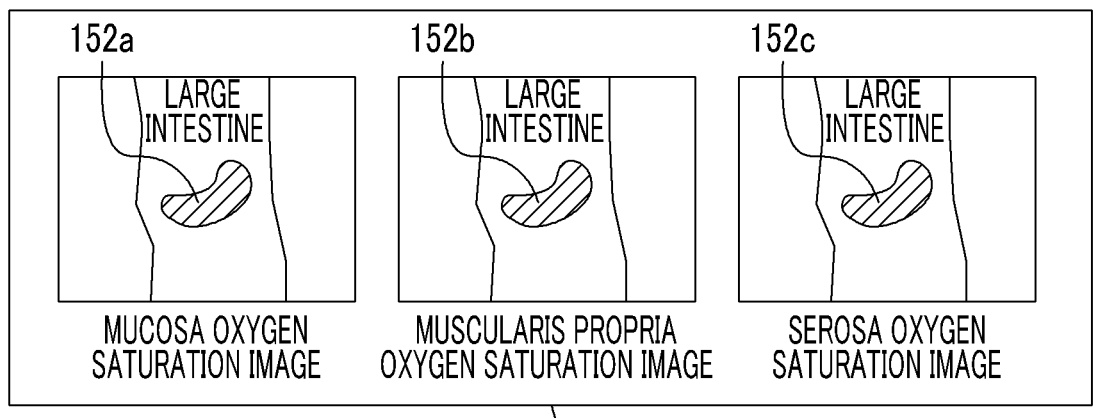
FIG. 28B is an image view showing a mucosa oxygen saturation image, a muscularis propria oxygen saturation image, and a serosa oxygen saturation image when the infiltration of the tumor is "T4".

For example, as shown in FIG. 28A, when it is determined that a low oxygen region 152a is present only in the mucosa oxygen saturation image and there is no low oxygen region in the muscularis propria oxygen saturation image and the serosa oxygen saturation image, "T1" indicating that the tumor has infiltrated to the mucosa is determined. On the other hand, as shown in FIG. 28B, when it is determined that low oxygen regions 152a to 152c are present in all of the mucosa oxygen saturation image, the muscularis propria oxygen saturation image, and the serosa oxygen saturation image, "T4" indicating that the tumor CN has infiltrated to the serosa is determined.

After determining the extent of infiltration from the three oxygen saturation images, the stage of the tumor CN is determined from the extent of lymph node metastasis and the extent of infiltration of the tumor. Based on the stage of the tumor, the resection range of the large intestine and blood vessels and lymph nodes connected to the large intestine are determined. The stages are "0", "I", "II", "III", and "IV". The larger the number, the greater the extent of progress of infiltration of the tumor. For example, when the extent of infiltration is "T1" or "T2" and the extent of lymph node metastasis is "N0" or "N1", the stage "I" is determined. In addition, when the extent of infiltration is "T4" and the extent of lymph node metastasis is "N2", the stage "IV" is determined.

Figure 29:
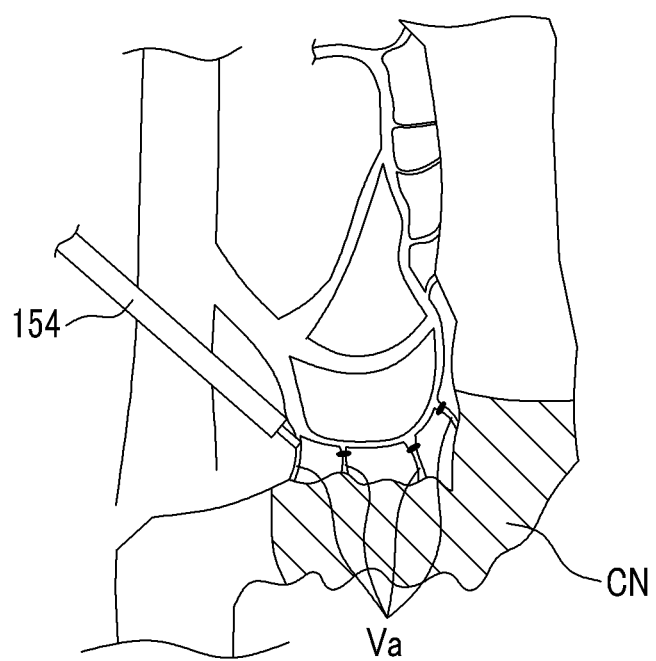
FIG. 29 is a diagram for explaining hemostasis.
Figure 30:
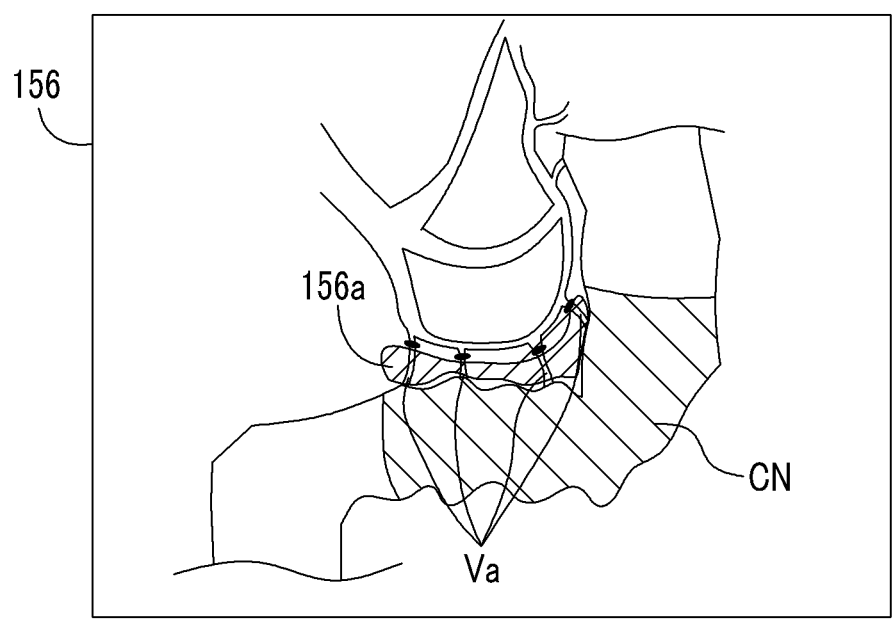
FIG. 30 is an image view of an oxygen saturation image showing the oxygen state of the surrounding tissues of an arterial blood vessel Va in which blood flow has stopped.

When the resection range is only the large intestine with a tumor, the arterial blood vessel Va of the tumor connected to the large intestine is cauterized and the flow of blood is stopped by using a hemostatic probe 154, as shown in FIG. 29. After the hemostasis, it is checked whether or not blood flow has stopped completely. As shown in FIG. 30, when the surrounding tissue of the arterial blood vessel Va in which blood flow has stopped is displayed as a low oxygen region 156a in an oxygen saturation image 156, the arterial blood vessel Va is in an ischemic state. The reason why the arterial blood vessel Va is in an ischemic state is that the new blood is not supplied to the arterial blood vessel Va. In this case, it can be thought that blood flow has stopped completely. In contrast, when the surrounding tissue of the arterial blood vessel Va is not displayed as the low oxygen region 156a in the oxygen saturation image 156, it can be thought that the new blood is continuously supplied to the arterial blood vessel Va. In this case, since the hemostasis is not sufficient, hemostasis using the hemostatic probe 154 is performed again. After confirming the complete hemostasis, the tumor CN is resected with an automatic suturing device.

Figure 31:
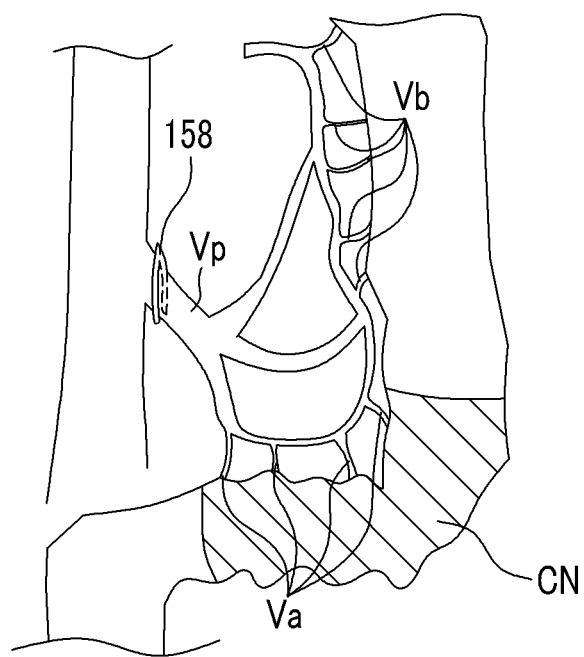
FIG. 31 is an image view of an oxygen saturation image in which arterial blood vessels Va and Vb, in which the flow of blood has been blocked by blocking forceps, are displayed.

On the other hand, when the resection range includes not only the tumor CN but also the arterial blood vessel Va and the lymph nodes connected to the tumor CN, blocking forceps 158 are first attached to an upstream-side arterial blood vessel Vp that is located on the upstream side of the arterial blood vessel Va, as shown in FIG. 31. As a result, the flow of blood to the arterial blood vessel Va is blocked. Here, after checking whether or not the arterial blood vessel Va is in a low oxygen state in the oxygen saturation image, hemostasis of the arterial blood vessel Va using the hemostatic probe 154 is performed in the same manner as described above. Then, after confirming that the arterial blood vessel on the tumor side is in an ischemic state, the arterial blood vessel Va and lymph nodes are resected with an electric scalpel, and the tumor CN is resected with an automatic suturing device.

Figure 32:
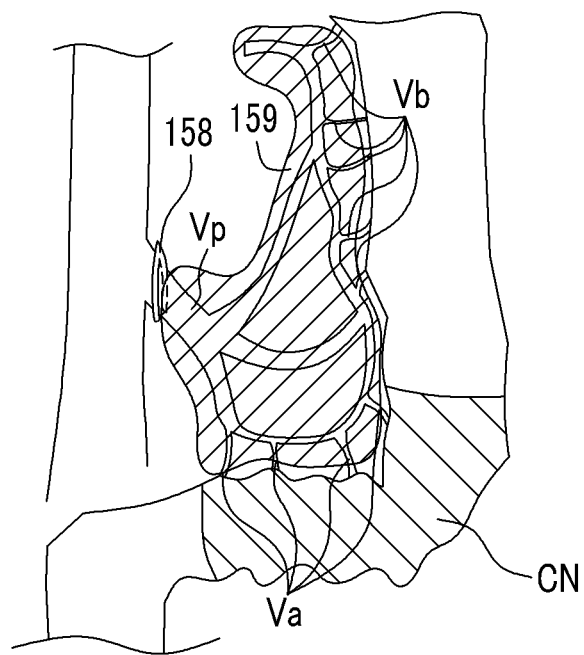
FIG. 32 is an image view of an oxygen saturation image showing the oxygen state of the surrounding tissues of arterial blood vessels Va and Vb.

In addition, when the arterial blood vessel Vp on the upstream side branches off not only to the arterial blood vessel Va on the tumor side but also to the arterial blood vessel Vb on the normal part side that is different from the tumor side, the flow of blood to the arterial blood vessel Vb on the normal part side is also blocked. That is, as shown in FIG. 32, not only the surrounding tissue of the arterial blood vessel Va on the tumor side but also the surrounding tissue of the arterial blood vessel Vb on the normal part side becomes a low oxygen region 159. In this case, if the low oxygen state in the surrounding tissue of the arterial blood vessel Vb on the normal part side continues for a long time, damage of the normal part is increased.

Figure 33:
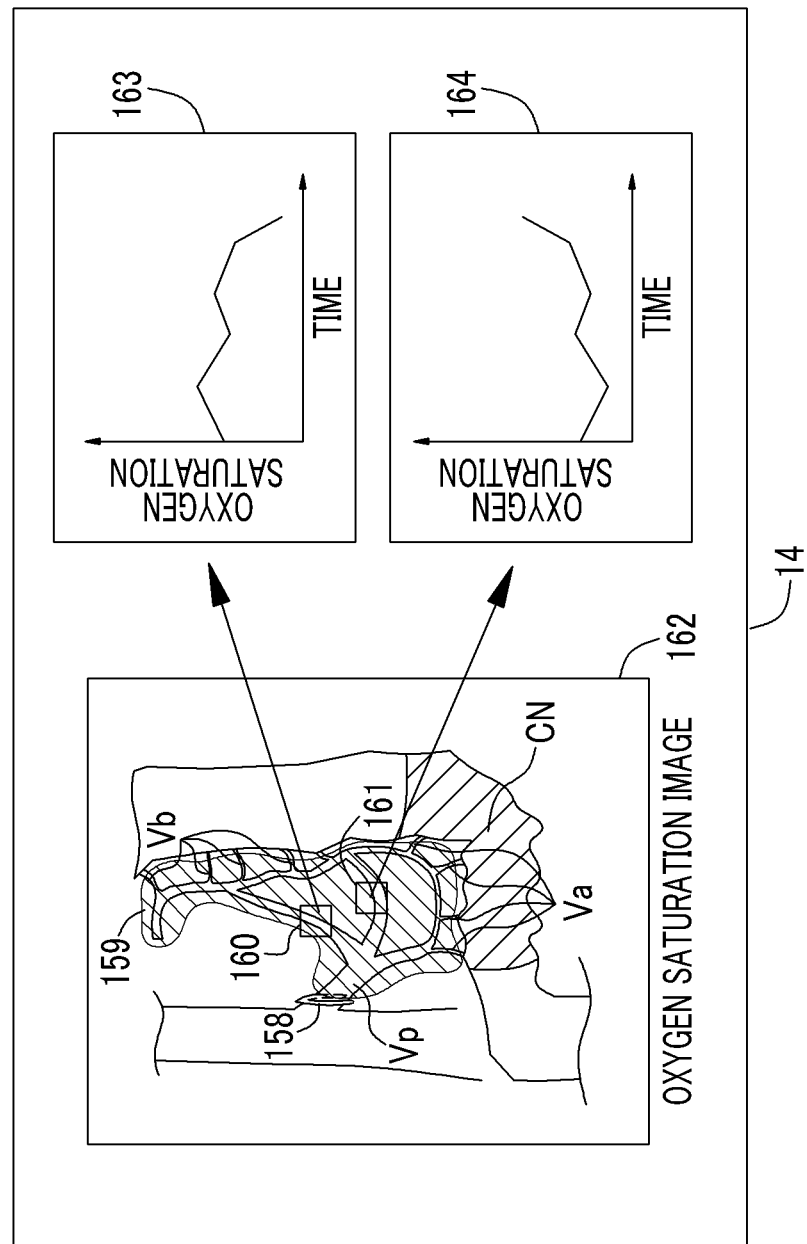
FIG. 33 is an image view of a monitoring image for monitoring the oxygen state of a plurality of regions of interest set in the arterial blood vessel Vb.

Therefore, in order to minimize the damage of the normal part, as shown in FIG. 33, regions of interest 160 and 161 are set in several places of the arterial blood vessel Vb on the normal part side, and the oxygen states in the regions of interest are monitored. The oxygen states in the regions of interest are displayed in graphs 163 and 164 next to an oxygen saturation image 162 on the display device 14. In the graphs 163 and 164, the vertical axis indicates oxygen saturation, and the horizontal axis indicates time. When the oxygen saturation is less than a predetermined threshold value in at least one place, a warning message (not shown) is displayed on the display device 14.

Figure 34:
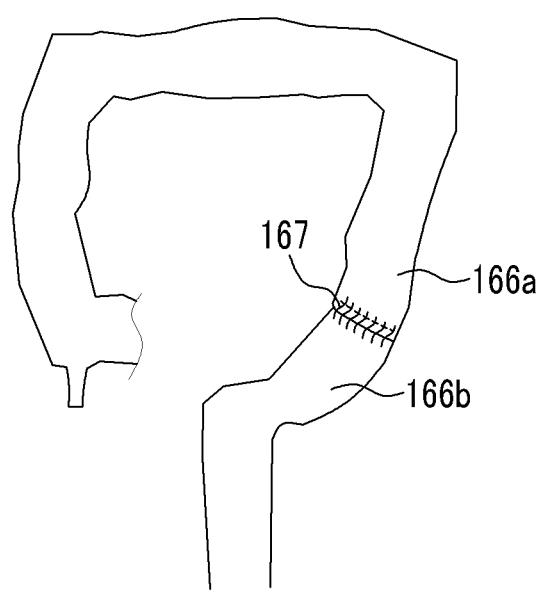
FIG. 34 is a plan view of the large intestine sutured by a suturing member.

After resecting the tumor and the like, the tumor CN and the like are brought close to the tip portion 105 of the abdominal cavity endoscope apparatus. Then, the tumor CN and the like and the abdominal cavity endoscope apparatus 101 are taken out through the trocar 110. After taking out the tumor CN, the abdominal cavity endoscope apparatus 101 is inserted again into the abdominal cavity. Then, as shown in FIG. 34, suturing between parts 166a and 166b of the large intestine separated due to the resection of the tumor CN is performed using an automatic suturing device (not shown). Examples of a suturing member 167 used for suturing between parts of the large intestine include surgical sutures and titanium staples. After the suturing between the parts of the large intestine, the abdominal cavity endoscope apparatus 101 and various treatment tools are removed, and then the trocars 109 and 110 are also removed.

The fusion check flow is performed within two to five days after surgery. In general, for the fusion between tissues connected together by the suturing member 167, approximately seven days is required after surgery. Therefore, it is preferable to check whether or not the tissues are activated within the period of the first two to five days out of the approximate seven days. If the tissues are not activated within the period, that is, if the tissue of the sutured portion is in a low oxygen state, the possibility of suture failure is high. Therefore, within the period of two to five days, it is checked whether or not the tissue of the sutured portion falls into the low oxygen state using the oxygen saturation image.

Figure 35:
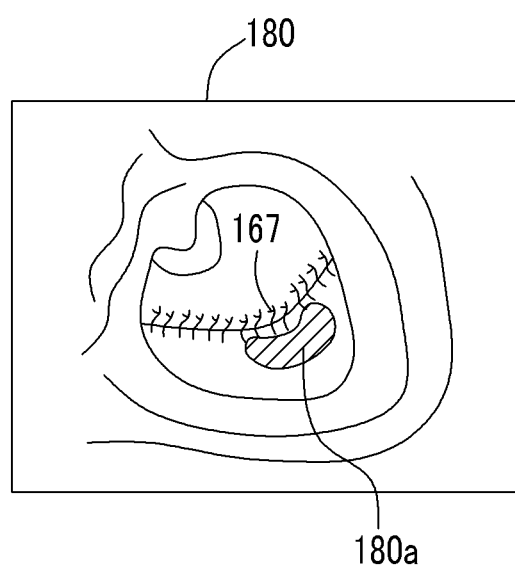
FIG. 35 is an image view of an oxygen saturation image showing the oxygen state of the large intestine on the luminal side sutured by the suturing member.

First, the luminal cavity endoscope apparatus 12 is inserted into the large intestine through the anus. Then, the luminal cavity endoscope apparatus is inserted up to the sutured portion. When the luminal cavity endoscope apparatus reaches the sutured portion, switching to the oxygen saturation mode is performed. As a result, an oxygen saturation image 180 shown in FIG. 35 is displayed on the display device 14. Then, the operator checks whether or not a low oxygen region 180a is present in the oxygen saturation image 180. If the low oxygen region 180a (region that has an oxygen saturation in a certain range (for example, 0% to 60%) set in advance and that is displayed in pseudo-color (for example, blue) which is different from the color of the normal image) is found, suturing is performed again using the abdominal cavity endoscope apparatus 101 since the possibility of suture failure is high. After checking the suture state, the luminal cavity endoscope apparatus 12 is removed from the large intestine.

In the fusion check flow, switching to the fusion check may be performed instead of switching to the oxygen saturation mode. In this case, the surface layer oxygen saturation image, the medium-deep layer oxygen saturation image, and the deep layer oxygen saturation image are displayed in parallel on the display device 14. Then, based on the three oxygen saturation images, the operator determines whether or not tissues are in a high oxygen state, that is, whether or not the tissues of the respective layers are activated.

Figure 36A:
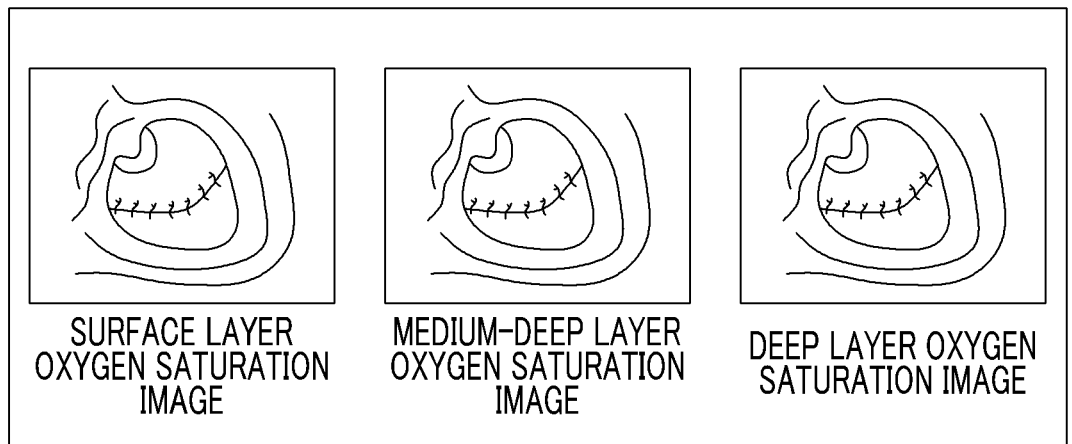
FIG. 36A is an image view of a surface layer oxygen saturation image, a medium-deep layer oxygen saturation image, and a deep layer oxygen saturation image when re-suturing is not required.
Figure 36B:
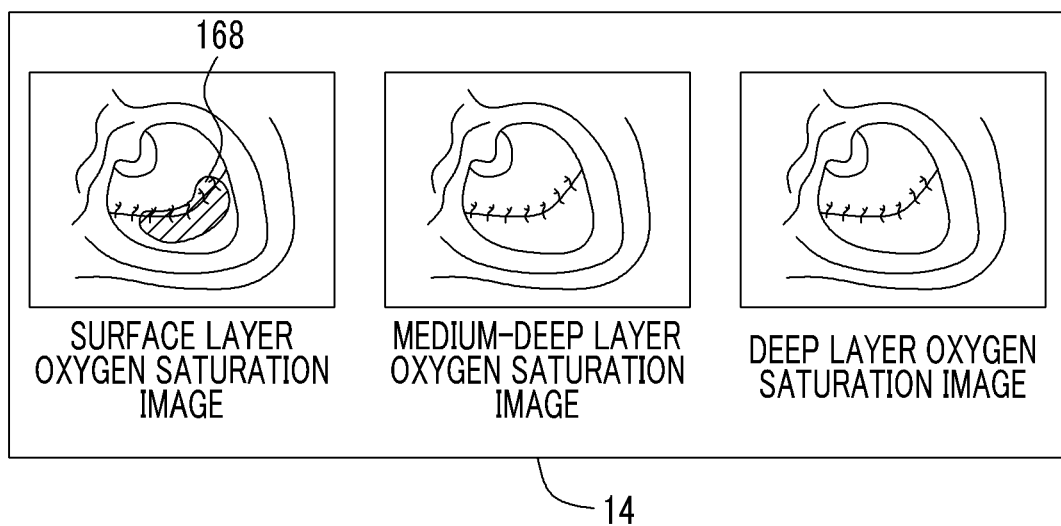
FIG. 36B is an image view of a surface layer oxygen saturation image, a medium-deep layer oxygen saturation image, and a deep layer oxygen saturation image when re-suturing is required.

For example, as shown in FIG. 36A, when there is no low oxygen region in the surface layer oxygen saturation image, the medium-deep layer oxygen saturation image, and the deep layer oxygen saturation image, it is thought that the tissues of all of the layers have been activated. In this case, since the fusion between the tissues is completed in a few days, the operator does not need to perform suturing again. In contrast, as shown in FIG. 36B, when there is no low oxygen region 168 in the medium-deep layer oxygen saturation image and the deep layer oxygen saturation image but the low oxygen region 168 is present in the surface layer oxygen saturation image, it is thought that the fusion between the tissues of the medium-deep layer and the deep layer will not be complete even if a few days pass. That is, the possibility of suture failure is high. In this case, the operator performs suturing again using the abdominal cavity endoscope apparatus 101. After checking the suture state, the luminal cavity endoscope apparatus 12 is pulled out from the large intestine.

Figure 37:
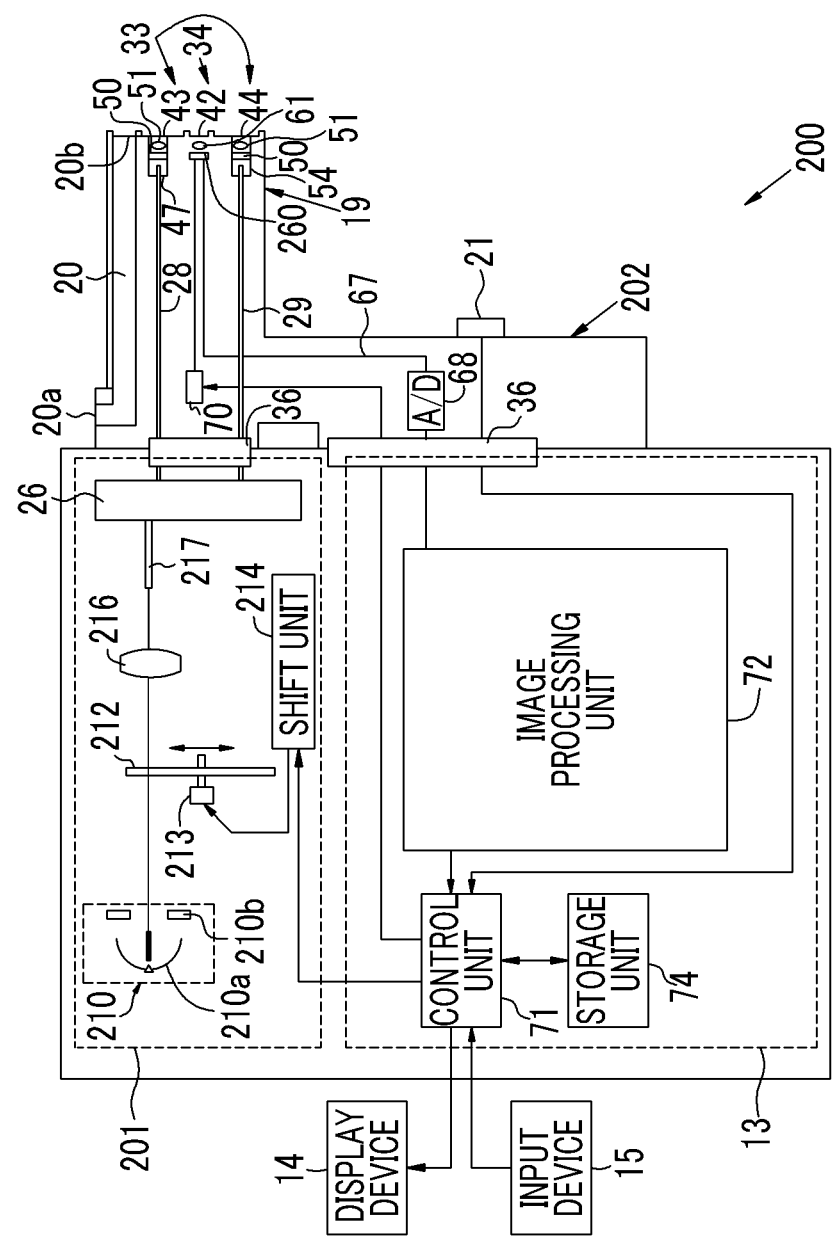
FIG. 37 is a block diagram of a luminal cavity endoscope system of a second embodiment.

Unlike the luminal cavity endoscope system 3 and the abdominal cavity endoscope system 4 adopting the semiconductor light source method, a medical apparatus system of a second embodiment is configured to include a luminal cavity endoscope system and an abdominal cavity endoscope system adopting a frame sequential method using a broadband light source, such as a xenon lamp. Hereinafter, a luminal cavity endoscope system 200 of the second embodiment shown in FIG. 37 will be described only for the differences from the first embodiment, and explanation regarding parts common to the luminal cavity endoscope system 3 of the first embodiment will be omitted. In addition, since the abdominal cavity endoscope system of the second embodiment is similar to the luminal cavity endoscope system, explanation thereof will be omitted.

A luminal cavity endoscope apparatus 201 of the luminal cavity endoscope system 200 is different from the luminal cavity endoscope apparatus 12 in that the fluorescent body 50 is not provided in the illumination unit 33 of the scope tip portion. Therefore, light from a luminal cavity light source device 201 is emitted to the inside of the subject through the light guides 28 and 29. In addition, unlike the imaging device 60, an imaging device 260 is a monochrome CCD in which no color filter is provided on the imaging surface. Other than these, a luminal cavity endoscope apparatus 212 has the same configuration as the luminal cavity endoscope apparatus 12.

The luminal cavity light source device 201 includes a white light source 2110 that emits broadband light BB (400 nm to 700 nm), a rotary filter 212 for wavelength separation of the broadband light BB from the white light source 210 to light having a predetermined wavelength, a motor 213 that is connected to the rotary shaft of the rotary filter 212 and rotates the rotary filter 212 at a fixed rotation speed, and a shift unit 214 for shifting the rotary filter 212 in the radial direction.

The white light source 210 includes a light source body 210a for emitting the broadband light BB and a diaphragm 210b for adjusting the amount of broadband light BB. The light source body 210a is a xenon lamp, a halogen lamp, or a metal halide lamp, for example. The aperture of the diaphragm 210b is adjusted by a light control unit (not shown).

Figure 38:
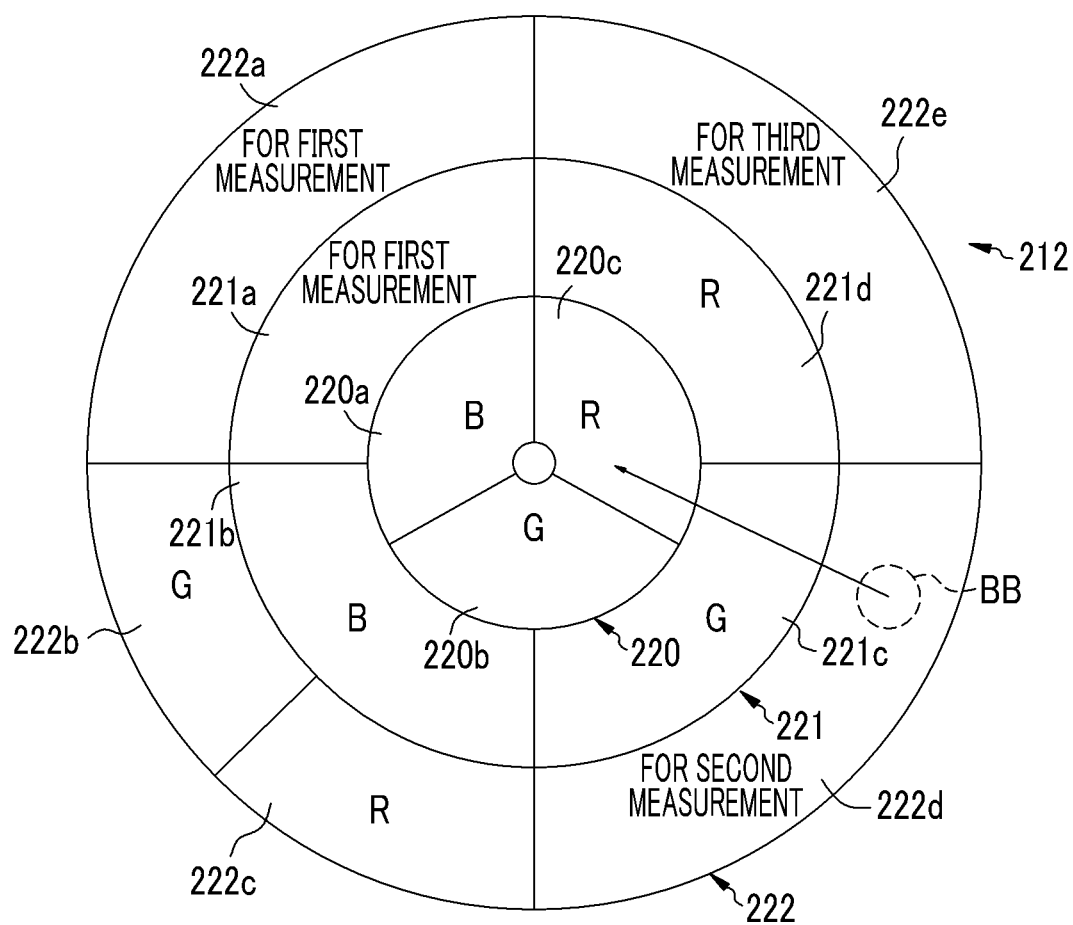
FIG. 38 is a plan view of a rotary filter.

As shown in FIG. 38, the rotary filter 212 rotates with a rotary shaft 212a connected to the motor 213 as the center of rotation. In the rotary filter 212, first to third filter regions 220 to 222 are provided, in order from the center of rotation where the rotary shaft 212a is located, along the radial direction. The first filter region 220 is set on the optical path of the broadband light BB in the normal mode, the second filter region 221 is set on the optical path of the broadband light BB in the oxygen saturation mode, and the third filter region 212 is set on the optical path of the broadband light BB in the fusion check mode. Switching of the filter regions 220 to 222 is performed by shifting the rotary filter 212 in the radial direction using the shift unit 214.

Figure 39:
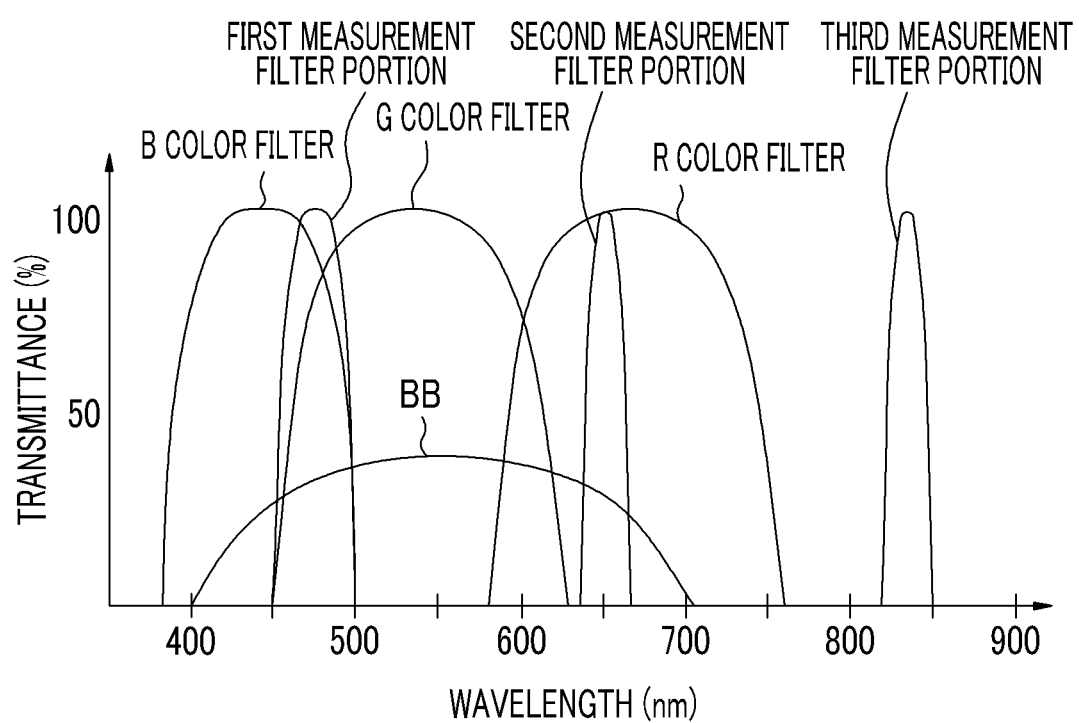
FIG. 39 is a graph showing the spectral transmittance of each filter portion of the rotary filter.

The first filter region 220 has a B filter portion 220a, a G filter portion 220b, and an R filter portion 220c, each of which is provided in a fan-shaped region of the central angle of 120°. As shown in FIG. 39, the B filter portion 220a transmits the broadband light BB and B light in a blue band (380 nm to 500 nm), the G filter portion 220b transmits the broadband light BB and G light in a green band (450 nm to 630 nm), and the R filter portion 220c transmits the broadband light BB and R light in a red band (580 nm to 760 nm). Accordingly, B light, G light, and R light are sequentially emitted by the rotation of the rotary filter 212. The B light, G light, and R light are incident on light guides 28 and 29 through a condensing lens 216 and an optical fiber 217.

In the second filter region 221, a first measurement filter portion 221a (written as "for first measurement" in FIG. 38), a B filter portion 221b, a G filter portion 221c, and an R filter portion 221d are provided. The first measurement filter portion 221a transmits first oxygen saturation measurement light in the wavelength range of 450 nm to 500 nm of the broadband light BB. In addition, the B filter portion 221b, the G filter portion 221c, and the R filter portion 221d transmit B light, G light, and R light, respectively, similar to the above B, G, and R filter portions 220a, 220b, and 220c. Accordingly, the first oxygen saturation measurement light, B light, G light, and R light are sequentially emitted by the rotation of the rotary filter 212. These four types of light are sequentially incident on the light guides 28 and 29 through the condensing lens 216 and the optical fiber 217.

In the third filter region 222, a first measurement filter portion 222a (written as "for first measurement" in FIG. 38), a G filter portion 222b, an R filter portion 222c, a second measurement filter portion 222d (written as "for second measurement" in FIG. 38), and a third measurement filter portion 222e (written as "for third measurement" in FIG. 38) are provided. The first measurement filter portion 222a transmits first oxygen saturation measurement light in the wavelength range of 450 nm to 500 nm of the broadband light BB.

In addition, the G filter portion 222b and the R filter portion 222c transmit G light and R light, respectively, similar to the above G and R filter portions 120b and 120c. The second measurement filter portion 222d transmits second oxygen saturation measurement light in the wavelength range of 640 nm to 660 nm of the broadband light BB, and the third measurement filter portion 222a transmits third oxygen saturation measurement light in the wavelength range of 830 nm to 850 nm of the broadband light BB. Accordingly, the first oxygen saturation measurement light, G light, R light, second oxygen saturation measurement light, and third oxygen saturation measurement light are sequentially emitted by the rotation of the rotary filter 212. These five types of light are sequentially incident on the light guides 28 and 29 through the condensing lens 216 and the optical fiber 217.

Figure 40A:
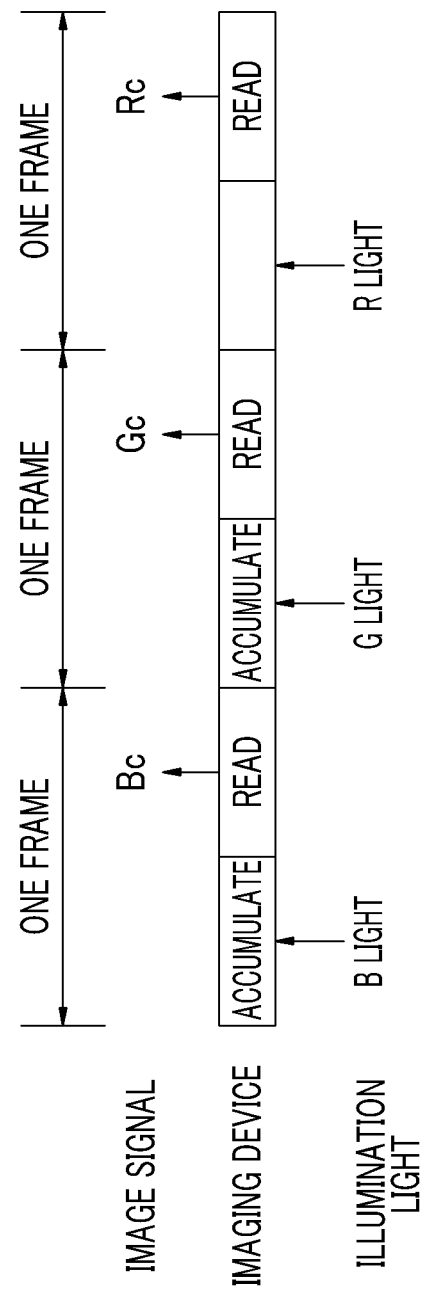
FIG. 40A is a diagram for explaining the imaging control in the normal mode in the second embodiment.

Since the luminal cavity endoscope system 200 of the second embodiment adopts the frame sequential method, the imaging control is different from the first embodiment. In the normal mode, as shown in FIG. 40A, image light beams of three colors of B, G, and R are sequentially imaged by an imaging device 103 and the electric charges are accumulated, and the blue signal Be, the green signal Gc, and the red signal Rc are sequentially output based on the accumulated electric charges. The series of operations are repeated while the normal mode is set. These signals Bc, Gc, and Rc of three colors are converted into blue image data Bc, green image data Gc, and red image data Rc, respectively, by the A/D converter 58. The image data Bc, Gc, and Rc approximately corresponds to the image data Be, Gc, and Rc in the first embodiment.

Figure 40B:
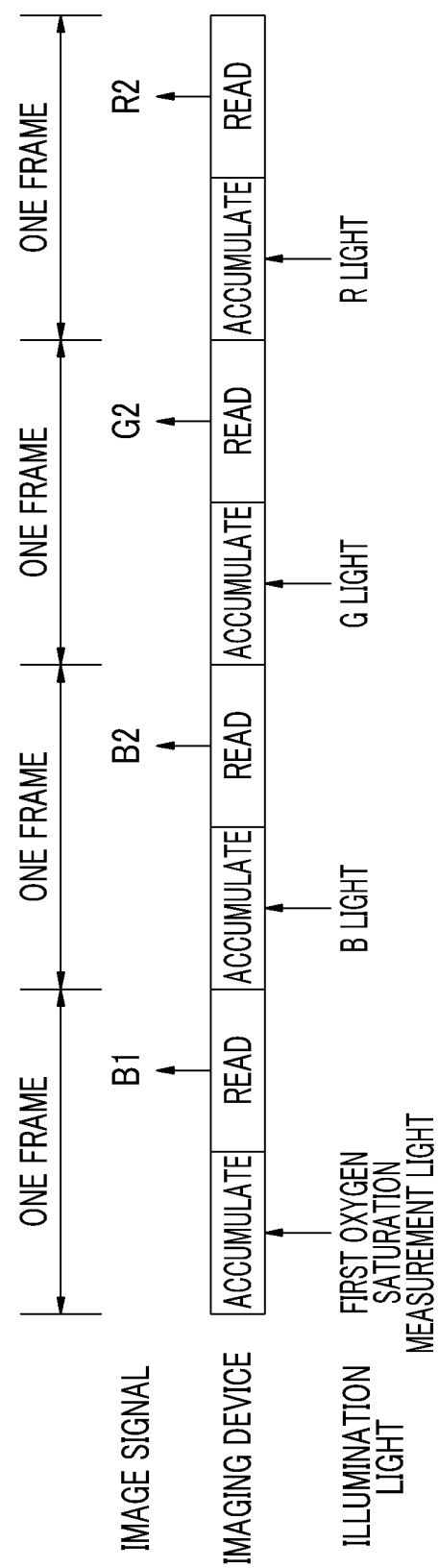
FIG. 40B is a diagram for explaining the imaging control in the oxygen saturation mode in the second embodiment.

In the oxygen saturation mode, as shown in FIG. 40B, the first oxygen saturation measurement light, B light, G light, and R light are sequentially imaged by the imaging device 103 and the electric charges are accumulated, and the blue signal B1, the blue signal B2, the green signal G2, and the red signal R2 are sequentially output based on the accumulated electric charges. Such an operation is repeated while the oxygen saturation mode is set. These signals B1, B2, G2, and R2 of four colors are converted into blue image data B1, blue image data B2, green image data G2, and red image data R2, respectively, by the A/D converter 58. The image data B1, B2, G2, and R2 approximately corresponds to the image data B1, B2, G2, and R2 in the first embodiment.

Figure 40C:
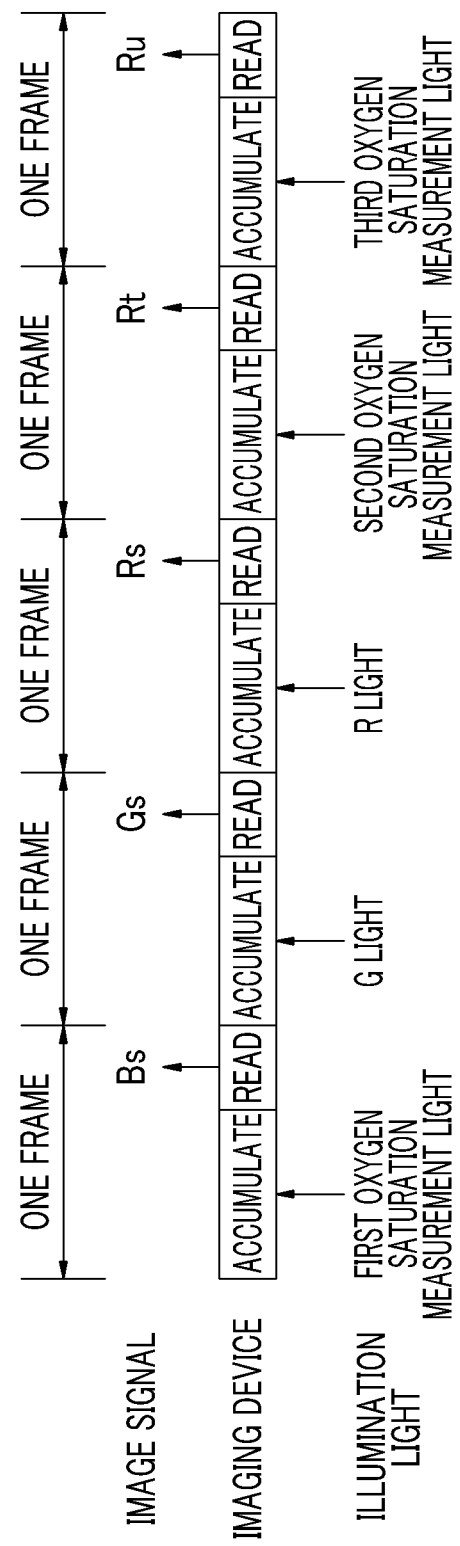
FIG. 40C is a diagram for explaining the imaging control in the fusion check mode in the second embodiment.

In the fusion check mode, as shown in FIG. 40C, the first oxygen saturation measurement light, G light, R light, second oxygen saturation measurement light, and third oxygen saturation measurement light are sequentially imaged by the imaging device 103 and the electric charges are accumulated, and the blue signal Bs, the green signal Gs, the red signal Rs, the red signal Rt, and the red signal Ru are sequentially output based on the accumulated electric charges. Such an operation is repeated while the oxygen saturation mode is set. These five signals Bs, Gs, Rs, Rt, and Ru are converted into blue image data Bs, green image data Gs, and red image data Rs, red image data Rt, and red image data Ru, respectively, by the A/D converter 58. The image data Bs, Gs, Rs, Rt, and Ru approximately corresponds to the image data Bs, Gs, Rs, Rt, and Ru in the first embodiment.

Figures 41A, 41B:
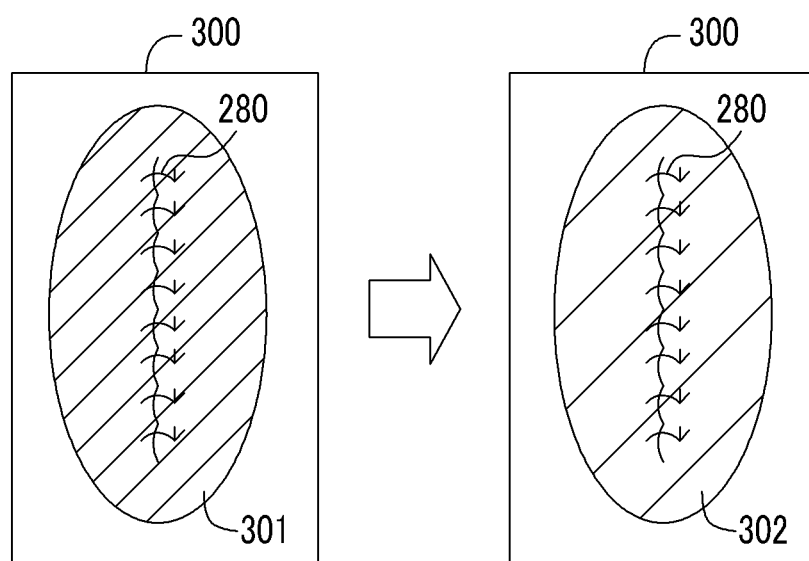
FIGS. 41A & 41B are image views showing an oxygen saturation image for checking the fusion state from the abdominal cavity side.

In the embodiment described above, using the luminal cavity endoscope apparatus, the fusion state between the tissues of the large intestine connected together by suturing has been determined from the luminal side. However, instead of this, using the abdominal cavity endoscope, the fusion state between the tissues may be determined from the abdominal cavity side. For example, as shown in FIG. 41A, immediately after suturing, a region around the tissues of the large intestine sutured by a suturing member 280 is not activated. Accordingly, the region is displayed as a low oxygen region 301 in an oxygen saturation image 300. However, when suturing has been done reliably, the sutured tissues are displayed as a high oxygen region 302 in the oxygen saturation image 300 after a few days has passed, as shown in FIG. 41B.

In the embodiment described above, as marking when identifying the location of the tumor, the method of pressing blood vessels around the tumor with a clip so that the blood vessels become ischemic has been used. However, it is possible to use a method of cauterization of blood vessels using hemostatic probe so that the blood vessels become ischemic or a method of inserting a catheter into a thick blood vessel around the tumor perimeter so that the thick blood vessel becomes occluded or ischemic.

Figure 42:
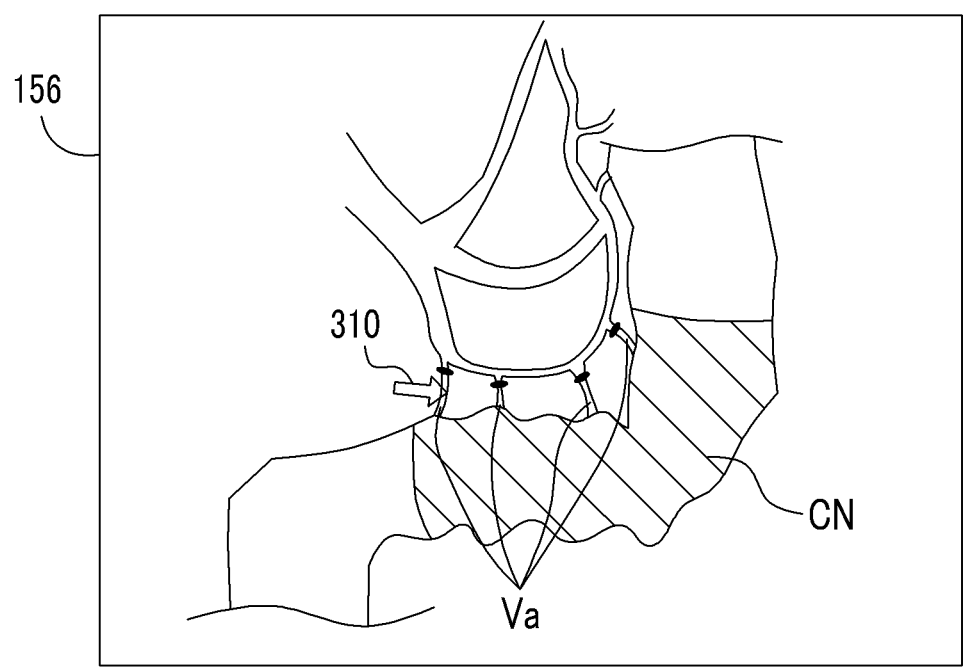
FIG. 42 is a diagram for explaining the automatic determination of the hemostatic state.

In the embodiment described above, during the hemostasis, the operator determines whether or not blood flow has stopped through the oxygen saturation image. However, the hemostatic state may also be automatically determined by the abdominal cavity processor device 102. In this case, as shown in FIG. 42, the operator or the like designates the blood vessel Va in which blood flow has stopped using a pointer 310 displayed in the oxygen saturation image 156. The designation of the blood vessel Va is performed by the input device 15.

When the oxygen saturation of the blood vessel Va designated by the pointer 310 is equal to or less than a predetermined value, it is determined that blood flow has stopped completely since it is thought that the new blood is not supplied. In this case, the display of "hemostasis OK" is displayed on the display device 14. On the other hand, when the oxygen saturation of the blood vessel Va designated by the pointer 310 exceeds the predetermined value, it is determined that blood flow has not stopped completely since it is thought that the new blood is supplied. In this case, the display of "hemostasis NG" is displayed on the display device 14.

In the embodiment described above, the fluorescent body 50 is provided in the scope tip portion 19. However, instead of this, the fluorescent body 50 may also be provided in the luminal cavity light source device 11 or the abdominal cavity light source device 100. In this case, it is preferable to provide the fluorescent body 50 between the LD2 (445 nm) and the optical fiber 23 and to provide no fluorescent body 50 between the other laser light sources LD1, LD3, LD4 and the optical fibers 22, 24, and 25.

In addition, in the first embodiment described above, a color imaging device configured to include the pixels of additive three primary colors (B, G, and R) arranged in a matrix has been used. However, a color imaging device configured to include the pixels of subtractive three primary colors (Y, M, and C) arranged in a matrix may be used. In addition, the number of colors of pixels may be four or more.

In addition, in the embodiment described above, the oxygen saturation image has been generated using the oxygen saturation that is the ratio of oxygenated hemoglobin of the blood volume (sum of oxygenated hemoglobin and reduced hemoglobin). However, instead of or in addition to this, it is also possible to use an oxygenated hemoglobin index calculated from "blood volume×oxygen saturation (%)" or a reduced hemoglobin index calculated from "blood volume×(100−oxygen saturation) (%)".

The effect of the invention can also be obtained by the following technical ideas.

[Additional Item 1]

A surgery method including: an ischemia step of making a tissue in a subject fall into an ischemic state using a treatment tool; an imaging step of imaging the tissue in the ischemic state using imaging unit; an oxygen saturation distribution image generation step of generating an oxygen saturation distribution image showing an oxygen state of the tissue in the ischemic state based on image information obtained by the imaging unit; a display step of displaying the oxygen saturation distribution image on display unit; and a surgery step of resecting the tissue while observing the oxygen saturation distribution image.

[Additional Item 2]

In the surgery method according to additional item 1, the treatment tool is attached to a region around a tumor in a lumen, and the oxygen saturation distribution image is displayed when identifying a location of the tumor from an abdominal cavity side.

[Additional Item 3]

In the surgery method according to additional item 1 or 2, the treatment tool is at least one of a clip and a catheter for blood vessel occlusion.

[Additional Item 4]

In the surgery method according to any one of additional items 1 to 3, the treatment tool is used for hemostasis of a first blood vessel connected to a tumor, and the oxygen saturation distribution image is displayed when checking whether or not blood flow in the first blood vessel has stopped.

[Additional Item 5]

The surgery method according to any one of additional items 1 to 4 further includes a monitoring step of monitoring an oxygen state of a second blood vessel, which is not resected in the surgery step, of the tissue based on the image information obtained by the imaging unit.

[Additional Item 6]

In the surgery method according to any one of additional items 1 to 5, in the oxygen saturation distribution image generation step, the oxygen saturation distribution image is generated based on first image information, which includes wavelength components at which an absorption coefficient of oxygenated hemoglobin and an absorption coefficient of reduced hemoglobin are different, and second image information including wavelength components that are different from the wavelength components in the first image.

[Additional Item 7]

In the surgery method according to additional item 6, the oxygen saturation distribution image generation step includes an oxygen saturation calculation step of calculating an oxygen saturation of each pixel based on the first and second image information and an image generation step of generating the oxygen saturation distribution image based on the oxygen saturation.

[Additional Item 8]

In the surgery method according to any one of additional items 1 to 7, in the surgery step, a first tissue including the low oxygen region of the tissue is resected, and a second tissue that does not include the low oxygen region is not resected.

What is claimed is:

1. An endoscope system, comprising:
a treatment tool configured to make a tissue in a subject fall into an ischemic state;
an endoscope apparatus configured to image the tissue in the ischemic state and to obtain image information of the tissue in the ischemic state;
a processor device that generates an oxygen saturation distribution image being an image in which at least part of color of a normal image is changed and showing an oxygen state of the tissue in the ischemic state based on image information obtained by the endoscope apparatus, the normal image formed as a subject image of visible light; and
a display device that displays the oxygen saturation distribution image,
wherein the processor device determines whether or not blood flow in a designated first blood vessel has stopped based on the oxygen saturation distribution image, and
the display device displays a determination result of the processor device.

2. The endoscope system according to claim 1,
wherein the treatment tool is configured to attach to a region around a tumor in a lumen, and
the oxygen saturation distribution image is displayed when identifying a location of the tumor from an abdominal cavity side.

3. The endoscope system according to claim 2,
wherein the treatment tool is at least one of a clip and a catheter for blood vessel occlusion.

4. The endoscope system according to claim 3, wherein the processor device monitors an oxygen state of a second blood vessel, which is not resected during predetermined surgery, of the tissue based on the image information obtained by the endoscope apparatus.

5. The endoscope system according to claim 2,
wherein the treatment tool is used for hemostasis of the first blood vessel connected to a tumor.

6. The endoscope system according to claim 2, wherein the processor device monitors an oxygen state of a second blood vessel, which is not resected during predetermined surgery, of the tissue based on the image information obtained by the endoscope apparatus.

7. The endoscope system according to claim 2,
wherein the processor device generates the oxygen saturation distribution image based on first image information, which includes wavelength components at which an absorption coefficient of oxygenated hemoglobin and an absorption coefficient of reduced hemoglobin are different, and second image information including wavelength components that are different from the wavelength components in the first image.

8. The endoscope system according to claim 7,
wherein the processor device calculates an oxygen saturation of each pixel based on the first and second image information and generates the oxygen saturation distribution image based on the oxygen saturation.

9. The endoscope system according to claim 2, further comprising:
a light source device that emits illumination light toward the tissue in the ischemic state, the illumination light including light of a semiconductor light source and fluorescent light obtained by wavelength conversion of the light of the semiconductor light source,
wherein the endoscope apparatus images the tissue in the ischemic state with a color imaging device.

10. The endoscope system according to claim 1,
wherein the treatment tool is at least one of a clip and a catheter for blood vessel occlusion.

11. The endoscope system according to claim 10,
wherein the treatment tool is used for hemostasis of the first blood vessel connected to a tumor.

12. The endoscope system according to claim 10, wherein the processor device monitors an oxygen state of a second blood vessel, which is not resected during predetermined surgery, of the tissue based on the image information obtained by the endoscope apparatus.

13. The endoscope system according to claim 10,
wherein the processor device generates the oxygen saturation distribution image based on first image information, which includes wavelength components at which an absorption coefficient of oxygenated hemoglobin and an absorption coefficient of reduced hemoglobin are different, and second image information including wavelength components that are different from the wavelength components in the first image.

14. The endoscope system according to claim 13,
wherein the processor device calculates an oxygen saturation of each pixel based on the first and second image information and generates the oxygen saturation distribution image based on the oxygen saturation.

15. The endoscope system according to claim 1,
wherein the treatment tool is used for hemostasis of the first blood vessel connected to a tumor.

16. The endoscope system according to claim 1, wherein the processor device monitors an oxygen state of a second blood vessel, which is not resected during predetermined surgery, of the tissue based on the image information obtained by the endoscope apparatus.

17. The endoscope system according to claim 1,
wherein the processor device generates the oxygen saturation distribution image based on first image information, which includes wavelength components at which an absorption coefficient of oxygenated hemoglobin and an absorption coefficient of reduced hemoglobin are different, and second image information including wavelength components that are different from the wavelength components in the first image.

18. The endoscope system according to claim 17,
wherein the processor device calculates an oxygen saturation of each pixel based on the first and second image information and generates the oxygen saturation distribution image based on the oxygen saturation.

19. The endoscope system according to claim 1, further comprising:
a light source device that emits illumination light toward the tissue in the ischemic state, the illumination light including light of a semiconductor light source and fluorescent light obtained by wavelength conversion of the light of the semiconductor light source,
wherein the endoscope apparatus images the tissue in the ischemic state with a color imaging device.

20. The endoscope system according to claim 1,
wherein the endoscope apparatus images a subject, to which a plurality of illumination light beams in different wavelength bands are sequentially emitted, with a monochrome imaging device.

21. The endoscope system according to claim 1, wherein the display device displays the tissue in the ischemic state as a low oxygen region with an oxygen saturation in a certain range in the oxygen saturation distribution image.

22. The endoscope system according to claim 1, wherein the endoscope apparatus includes
a luminal cavity endoscope system with a flexible endoscope provided to a forceps channel for inserting the treatment tool;
an abdominal cavity endoscope system with a rigid endoscope configured to image the tissue made into the ischemic state by the treatment tool and to obtain image information of the tissue in the ischemic state;
the processor device that generates the oxygen saturation distribution image by the rigid endoscope.

* * * * *